United States Patent
Goldsberry et al.

(10) Patent No.: US 10,624,834 B2
(45) Date of Patent: Apr. 21, 2020

(54) SPHERE FORMING COMPOSITIONS

(71) Applicant: Benchmark Cosmetic Laboratories, Inc., Irvine, CA (US)

(72) Inventors: Susan Goldsberry, Newport Coast, CA (US); Lyndon S. Garcines, Fountain Valley, CA (US); Yen H. Ly, Fountain Valley, CA (US)

(73) Assignee: Benchmark Cosmetic Laboratories, Inc., Irvine, CA (US)

( * ) Notice: Subject to any disclaimer, the term of this patent is extended or adjusted under 35 U.S.C. 154(b) by 32 days.

(21) Appl. No.: 16/221,365

(22) Filed: Dec. 14, 2018

(65) Prior Publication Data

US 2019/0125654 A1 May 2, 2019

Related U.S. Application Data

(63) Continuation-in-part of application No. PCT/US2017/037690, filed on Jun. 15, 2017.

(60) Provisional application No. 62/351,798, filed on Jun. 17, 2016.

(51) Int. Cl.
| | |
|---|---|
| *A61K 8/891* | (2006.01) |
| *A61K 8/73* | (2006.01) |
| *A61Q 19/00* | (2006.01) |
| *A61K 8/11* | (2006.01) |
| *A61K 8/895* | (2006.01) |
| *A61K 8/02* | (2006.01) |
| *A61K 8/31* | (2006.01) |
| *A61K 8/34* | (2006.01) |
| *A61Q 5/12* | (2006.01) |

(52) U.S. Cl.
CPC .............. *A61K 8/891* (2013.01); *A61K 8/025* (2013.01); *A61K 8/11* (2013.01); *A61K 8/31* (2013.01); *A61K 8/345* (2013.01); *A61K 8/73* (2013.01); *A61K 8/895* (2013.01); *A61Q 5/12* (2013.01); *A61Q 19/00* (2013.01); *A61K 2800/30* (2013.01); *A61K 2800/48* (2013.01); *A61K 2800/524* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 9,433,564 B2 | 9/2016 | Choi et al. | |
| 9,498,430 B1 | 11/2016 | Choi et al. | |
| 2006/0153905 A1* | 7/2006 | Carrara | A61K 9/0014 424/449 |
| 2009/0104129 A1* | 4/2009 | Chen | A61K 8/4973 424/59 |
| 2015/0050321 A1 | 2/2015 | Gately et al. | |

FOREIGN PATENT DOCUMENTS

| | | |
|---|---|---|
| WO | 99011237 | 3/1999 |
| WO | 2017103083 | 6/2017 |
| WO | 2017137597 | 8/2017 |

OTHER PUBLICATIONS

International Search Report in WO 2017/218783, dated Sep. 12, 2017.
Written Opinion in WO 2017/218783, dated Sep. 12, 2017.

* cited by examiner

*Primary Examiner* — Robert A Wax
*Assistant Examiner* — Randeep Singh
(74) *Attorney, Agent, or Firm* — Transformative Legal, LLC; Len Smith; Denise Brown

(57) ABSTRACT

Disclosed is a composition that begins as a multi-phase structure including a plurality of immiscible liquids that, upon agitation, encapsulates and suspends one of the plurality of liquids (e.g., in spheres). In some embodiments, the composition includes a water phase and an anhydrous phase. The composition can include a thickener added to the water phase to allow the water molecules to encapsulate the anhydrous phase into spheres. The formed spheres are stable and can be configured to last for specific durations depending on modifications to the formula. In some embodiments, the spheres can release back into the multi-phase structure after a specific period of time. The formulations disclosed herein can act as a vehicle or a base formulation to which additional ingredients can be added. The disclosed formulation, in addition to enabling the intermixing of two immiscible liquids, can provide a number of additional benefits.

24 Claims, 3 Drawing Sheets

SPHERE FORMING COMPOSITIONS

This application is a continuation-in-part of PCT/US2017/037690, filed Jun. 15, 2017, which claims priority to U.S. provisional application 62/351,798, filed Jun. 17, 2016. Both applications are incorporated herein by reference in their entirety.

BACKGROUND

Field

This disclosure relates to solutions comprising two or more liquids that are normally immiscible, that can be intermixed to form spheres of one liquid encapsulated in another.

Description of the Related Art

Beauty products, such as skincare and haircare products, are frequently formulated using a mixture of oils and water which are immiscible. Common solutions involve using an emulsifier/solubilizer or creating "beads" or "shells" that require encapsulation materials. However, emulsifiers tend to be sticky and can create products with an undesirable tacky feel. As for the use of encapsulation materials, these can be hard to break and leave residue on the skin or hair.

SUMMARY

Disclosed herein are several embodiments of a composition made up of a plurality of immiscible liquids that, when agitated, form spheres that encapsulate at least one of the plurality of immiscible liquids.

In some embodiments, disclosed is a composition configured to form spheres when agitated. In some embodiments, the composition includes a water phase (the phrase "water phase" is synonymous herein with "aqueous phase") comprising between about 25 wt. % to about 90 wt. % of the composition, the water phase comprising: (i) water, comprising between about 60 wt. % to about 95 wt. %, (ii) a first gelling agent configured to alter the size and duration of the formed spheres, the first gelling agent comprising sclerotium gum and comprising between about 0.10 wt. % to about 1.50 wt. % of the water phase, (iii) a second gelling agent configured to suspend an anhydrous phase within the water phase, the second gelling agent comprising xanthan gum and comprising between about 0.10 wt. % to about 2.00 wt. % of the water phase, (iv) a skin conditioning agent configured to enhance the penetration of the composition into the skin, the skin conditioning agent comprising at least one of pentylene glycol, butylene glycol, and another water soluble skin conditioning agent and comprising between about 1.00 wt. % to about 5.00 wt. % of the water phase, and (v) a preservative comprising between about 0.20 wt. % to about 5.00 wt. %. In some embodiments, the composition includes an anhydrous phase comprising between about 10 wt. % to about 75 wt. % of the composition, the anhydrous phase comprising: a conditioning agent configured to set the size and duration of the formed spheres, the conditioning agent comprising at least one of isododecane, isohexadecane, Botanisil GB-21, and Botanisil GB-41, and comprising between about 5.00 wt. % to about 70.00 wt. % of the anhydrous phase.

In some embodiments, the composition is free of any film forming polymers or film-forming emulsifiers other than an ester emollient. In some embodiments, the composition is free of any carbomers. In some embodiments, the composition is free of emulsifying waxes. In some embodiments, the composition is free of lecithin. In some embodiments, the composition is free of stearates. In some embodiments, the composition is free of propylene glycol. In some embodiments, the composition is free of polysorbates. In some embodiments, the composition is free of polyethylene glycols. In some embodiments, the composition is free of lipophilic gelling agents. In some embodiments, the composition is free of polyacrylates.

In some embodiments, the composition contains no more than 0.5 wt. % of any cetearyl alcohol, mannitol, lactose or salt forms of a neutralized acid.

In some embodiments the composition contains an oil phase that is substantially free of water (e.g., contains no more than about 5 wt. %, no more than 2 wt. %, no more than 1 wt. %, no more than about 0.5 wt. %, no more than about 0.25 wt. %, no more than about 0.1 wt. %, or no more than about 0.001 wt. % water). In other embodiments the oil phase contains no detectable water (although the oil phase may be in contact with water in the aqueous phase at one or more interfaces depending on the state of the composition at any given time). Herein the term "anhydrous phase" can be used to indicate any such type of oil phase and the terms "oil phase" and "anhydrous phase" will be understood to generally be used interchangeably herein, while providing support for phases which are free of detectable amounts of water. Thus, in some embodiments, the term "anhydrous phase" or "oil phase" should be understood to indicate a phase essentially free of water.

In some embodiments, the oil phase and aqueous phase together make up at least 85 wt. % of the composition. In other aspects, the oil phase and aqueous phase together make up at least about 90%, at least about 95%, at least about 97.5%, at least about 99%, or at least about 100% of the composition. In some embodiments, the oil phase and aqueous phase make up the entirety of the composition, at least within levels of detectability and/or at least with respect to intended inputs to the composition.

In some embodiments, the first and second phases are in contact with one another and spontaneously form a first state in which the entirety of the first phase is separated from the second phase except at the interface of the first and second phases. In some embodiments, the first and second phases remain in a separated state unless provoked to mix through agitation.

In some embodiments, upon agitation, the oil phase and water phase are capable of forming a second state in which a majority of the anhydrous phase is suspended in a plurality of separated spherical portions within the aqueous phase, a majority of the spherical portions being capable of remaining stable for extended periods of time without further agitation. In some embodiments, the majority of the spherical portions are capable of remaining stable for at least one month without further agitation.

In some passages of the description provided herein numeric values are presented with decimal values of two significant figures (e.g., numeric values used to describe the weight percentage of element content within the composition). However, in some cases, such precision is not necessary and may lead to confusion about the scope of the disclosure and the invention. Accordingly, it should be understood that the use of "about" in conjunction with amounts provided with two significant digits after the decimal should be interpreted as if a single significant digit or no significant digits exist after the decimal, for example, the phrase "about 2.00%" should be understood to indicate an amount of, for example, 1.8%, 1.85%, 1.9%, 1.95%, 2%, 2.1% or 2.2% or 2.20%.

In other embodiments, the water phase has a pH between about 3.5 to about 8.0. In other embodiments, the water phase has a viscosity between about 500 to about 15,000 cps. In other embodiments, the aqueous phase has a viscosity of between about 1,000 to about 12,000 cps. In other embodiments, the aqueous phase has a viscosity of between about 2,000 to about 10,000 cps. In other embodiments, the anhydrous phase has a viscosity of between about 50 to about 10,000 cps. In some embodiments, the anhydrous phase has a viscosity of between about 50 to about 1,000 cps. In some embodiments, the anhydrous phase has a viscosity of between about 50 to about 500 cps. In some embodiments, the viscosity of the composition upon mixing may have a viscosity of between about 400 cps to about 38,000 cps. In other embodiments, the viscosity of the composition upon mixing may have a viscosity of between about 2,000 cps to about 30,000 cps. In other embodiments, the viscosity of the composition upon mixing may have a viscosity of between about 5,000 cps to about 25,000 cps. In some embodiments, the composition upon mixing may have a pH of about 3.0 to about 6.0, for example about 3.0 to about 6.0, about 3.5 to about 5.5, or about 3.5 to about 4.5.

Herein, the units "cps" represent the viscosity measurement centipoise. Viscosity may also be measured in centistokes or "cts". The viscosity values provided herein are represented in centipoise. One skilled in the art will recognize that the conversion of cps to commonly utilized units of cts may be performed by dividing by the density of the substance at hand. Therefore, for many elements and compositions described herein having a density of approximately 0.6-approximately 0.9 g/cm3, the values provided, plus or minus about 20% should be understood as being disclosed for each specific unit with respect to the other unit (e.g., a disclosure of a component with a viscosity of about 100 cts should be understood as disclosing 80-120 cps and vice versa).

In other embodiments, the composition includes a complexion brightener. In general, the complexion brightener can be any molecule or composition that is capable of detectably brightening the complexion of a substantial number of users of the molecule or composition, especially in the context of the composition of the invention to which it is added. According to particular embodiments, the complexion brightener comprises at least one of Neurocap, brightenyl, niacinamide, SpecWhite® Plus, or copper derivative (in some embodiments having the trade name Neodermyl, available from Induchem), or a mixture of some or all thereof.

The composition can also or alternatively comprise other functional components, additional examples of which will be described herein. According to embodiments, an advantage of compositions of the invention is the ability to incorporate one or more functional components (e.g., retinoids, vitamins, mica, peptides, extracts, and other functional/active ingredients, including complexion brighteners or colorants) in the composition stably without loss of the ability of the composition to form the second state (e.g., a state in which at least a substantial proportion of the oil phase, such as 50% or more, 66.6% or more, 75% or more, 85% or more, 90% or more, 95% or more, or 99% or more of the oil phase is suspended in spheres in the water phase) and to maintain the stability of the second state after agitation for a desired period of time (e.g., at least 1 week, at least 2 weeks, at least one month, at least 2 months, at least 3 months, at least 4 months, at least 6 months, at least 9 months, at least 12 months, at least 18 months, at least 24 months, at least 30 months, at least 36 months, or even longer, such as 42 months or longer). A functional component can be any composition or molecule that imparts a functionality or activity to the composition, preferably in or at the surface of the skin when a composition is applied topically. A functional component may impart moisture, firmness, color, or delivery of active compounds such as pharmaceutically active ingredients.

In some embodiments, the aqueous phase of the composition comprises a water-soluble acid. In some embodiments, water-soluble acid is an alpha hydroxy acid. In some embodiments, the composition includes an alpha hydroxyl acid configured to help break down the spheres formed by the composition. In some embodiments, the water-soluble acid is capable of detectably extending the time the composition is maintained in the second phase following agitation. In other embodiments, the alpha hydroxyl acid comprises at least one of glycolic acid or lactic acid. In other embodiments, the alpha hydroxyl acid comprises between about 0.10% to about 20.00% by weight of the water phase.

In some embodiments the composition is free of proteins or peptides, or at least free of proteins comprising more than one peptide chain (e.g., is free of any dimers or multimers) or single chain proteins or peptides comprising more than about 100 amino acids, more than about 80 amino acids, more than about 50 amino acids, or even more than about 25 amino acids. In some embodiments the composition is free of algae products or macroalgae and/or microalgae products, such as extracts obtained from such organisms or compositions produced from such organisms. In other contexts, the composition can also or alternatively be characterized in being free of a biologically and/or chemically active protein, such as an enzyme.

In other embodiments, the composition includes an inorganic salt configured to neutralize the glycolic acid in the composition. In other embodiments, the inorganic salt comprises at least one of sodium hydroxide or aminomethyl propanol. In other embodiments, the inorganic salt comprises between about 0.20% to about 4.00% of the water phase.

In other embodiments, the preservative comprises propanediol.

In some embodiments the composition comprises one or more silicone elements having a viscosity ranging between 5 cps and 500,000 cps.

In other embodiments, the conditioning agent comprises or is combined with at least one of dimethicone or a dimethicone crosspolymer.

In other embodiments, the anhydrous phase comprises at least one of dimethicone, a dimethicone crosspolymer, cyclopentasiloxane, a cyclopentasiloxane blend, cyclohexasiloxane, cyclotetrasiloxane, cycloheptasiloxane, and phenyl trimethicone. In other embodiments, at least one of cyclopentasiloxane, cyclohexasiloxane, cyclotetrasiloxane, and cycloheptasiloxane comprises between about 10.00 wt. % to about 100.00 wt. % of the anhydrous phase (e.g., about 20-100 wt. %, such as about 25-100 wt. %, about 33-100 wt. %, about 40-100 wt. %, about 25-95 wt. %, about 33-99 wt. %, about 40-95 wt. %, about 40-90 wt. %, about 50-100 wt. %, about 50-95 wt. %, or about 65-100 wt. % or about 65-95 wt. %). In some embodiments, the majority of the conditioning component and/or emollient component is composed of one or more silicone emollients.

In some embodiments, a silicone element (emollient) is the only conditioning agent (or agent in the emollient component) in the anhydrous phase of the composition. In other embodiments, the silicone element or silicone emollient component may be replaced in whole or in part by an ester emollient, several examples of which are provided herein. Often the silicone component will be supplemented by an ester emollient. In such cases the amount of the silicone emollient or silicone element may be reduced by about 10-70%, such as about 15-65%, such as about 20-60%, with the balance made up of an ester emollient. In some embodiments, the silicone element or silicone emollient component or also or alternatively the ester emollient may have a density of about 0.6-0.9 g/cm3.

In certain embodiments the composition is characterized in comprising an emollient component. In other embodiments, the composition is also or alternatively described as comprising a conditioning agent (which is also sometimes called a conditioning component). In most cases the compositions described as suitable components of the conditioning agent will also be suitable components of the emollient component or both the emollient component and the hydrocarbon component of embodiments that are described as comprising both an emollient component and a hydrocarbon component. For example, BIOSIL compositions, which can be suitable conditioning agents, also can contribute to or provide both a silicone emollient and a hydrocarbon component (isododecane). Accordingly, the respective disclosures provided herein with respect conditioning agents, emollient components, and hydrocarbon components will be understood as being generally interchangeable as exemplified here and as will be clear from other portions of the disclosure.

In still other aspects of the invention the emollient component comprises a mixture of an ester emollient portion, such as a MIGLYOL emollient or a mixture thereof (examples of which are described elsewhere herein), and one or more silicone emollients, such as one or more of a dimethicone or a dimethicone crosspolymer. In other embodiments the composition comprises either a silicone emollient or an ester emollient.

In other embodiments, the spheres formed when the composition is agitated have a diameter between approximately 0.5 to approximately 5 mm. In other embodiments, the spheres stay formed for at least 30 minutes. In other embodiments, the spheres stay formed for at least 1 hour. In other embodiments, the spheres stay formed for at least 2 hours. In other embodiments, the spheres stay formed for at least 8 hours. In other embodiments, the spheres (e.g., at least 50% of the spheres, such as at least 75% of the spheres, or at least 90% of the spheres) stay formed for at least 6 months from initial sphere formation (agitation) when the composition is maintained at about room temperature (without need for further agitation or stabilization). In other embodiments, similar amounts of the spheres stay formed for at least 1 year. In other embodiments, spheres stay formed for at least 2 years. In yet further embodiments, spheres stay formed for at least 42 months.

According to embodiments, disclosed are topical compositions that are configured to form spheres when agitated. In some embodiments, the composition comprises a water phase comprising: (i) water, (ii) a first gelling agent configured to alter the size and duration of the formed spheres, (iii) a second gelling agent configured to suspend the anhydrous phase within the water phase, (iv) a skin conditioning agent configured to enhance the penetration of the composition into the skin, and (v) a preservative. In some embodiments, the composition comprises an anhydrous phase comprising: a conditioning agent configured to set the size and duration of the formed spheres.

In other embodiments, water can compose between about 60 wt. % to about 95 wt. % of the water phase. In other embodiments, the anhydrous phase makes up between about 10 wt. % to about 75 wt. %, for example about 20 wt. % to about 50 wt. %, 25% to about 45 wt. %, and in other cases about 30% to about 40% by weight of the topical composition. In other embodiments, the water phase makes up between about 25 wt. % to about 90 wt. % of the topical composition. In other embodiments, the water phase has a pH between about 3.5 to about 8.0. In other embodiments, the water phase has a viscosity between about 500 to about 15,000 cps. In other embodiments, the anhydrous phase has a viscosity between about 50 to about 10,000 cps.

In other embodiments, the first gelling agent comprises sclerotium gum. In other embodiments, the sclerotium gum comprises between about 0.10 wt. % to about 1.50 wt. % of the water phase. In other embodiments, the sclerotium gum comprises between about 0.15 wt. % to about 1.5 wt. % In other embodiments, the second gelling agent comprises xanthan gum. In other embodiments, the xanthan gum comprises between about 0.10 wt. % to about 2.00 wt. % of the water phase.

In other embodiments, the skin conditioning agent is water soluble. In some embodiments the composition comprises a glycol. In some embodiments, the glycol is incorporated in an amount that is capable of detectably improving the absorption of the composition into the skin when applied topically. In some embodiments, when glycol is present, about 95% or more of an amount of the composition between about 0.025-0.075 mL is capable of being absorbed into the skin within one minute of topical application. In some embodiments such a result is attainable without rubbing. In some embodiments, such an application leaves no detectable residue on the skin as reported by a majority of users in a product test. In other embodiments, the skin conditioning agent comprises at least one of pentylene glycol, butylene glycol, and another water-soluble skin conditioning agent. In other embodiments, the skin conditioning agent comprises between about 1.00 wt. % to about 5.00 wt. % of the water phase.

In other embodiments, the composition includes a complexion brightener. In other embodiments, the complexion brightener comprises at least one of Neurocap, Brightenyl®, niacinamide, Specwhite® Plus, or copper derivative.

In other embodiments, the composition includes an alpha hydroxyl acid configured to help break down the spheres formed by the topical composition. In other embodiments, the alpha hydroxyl acid comprises at least one of glycolic acid or lactic acid. In other embodiments, the alpha hydroxyl acid comprises between about 0.10% to about 20% by weight of the water phase.

In other embodiments, the composition includes an inorganic salt configured to neutralize the glycolic acid in the topical composition. In other embodiments, the inorganic salt comprises at least one of sodium hydroxide or aminomethyl propanol. In other embodiments, the inorganic salt comprises between about 0.20% to about 4.00% of the water phase (e.g., about 0.5-3.5 wt. %, such as about 0.75-3 wt. %).

In general percentages provided herein are in reference to weight of either the composition or, if indicated, weight of a phase or component of the composition. As such, those of skill in the art will recognize the preceding disclosure of "about 0.20% to about 4.00% of the water phase" to mean about 2-4 wt. % of the aqueous phase. This understanding of percentage should be applied throughout this disclosure, except where explicitly otherwise stated or clearly contradicted by context.

In other embodiments, the preservative is water soluble and comprises between about 0.2% to about 5% of the water phase, e.g., about 0.25-2.5% of the water phase (e.g., about 0.5-2% of the water phase or about 0.75-1.5% of the water phase). In other embodiments, the preservative comprises propanediol. In other embodiments, the propanediol comprises between about 1.00% to about 5.00% of the water phase.

In other embodiments, the conditioning agent (which can comprise all or part of the hydrocarbon component, the emollient component, or both) comprises at least one of isododecane, isohexadecane, Botanisil GB-21, and Botanisil GB-41. In other embodiments, the conditioning agent is combined with at least one of dimethicone or a dimethicone crosspolymer. In other embodiments, the conditioning agent comprises between about 5.00 wt. % to about 70.00 wt. % of the anhydrous phase (e.g., about 6.5-65 wt. %, such as about 10-50 wt. % of the oil phase). In other embodiments, the conditioning agent makes up at least 4 wt. % of the oil phase.

In other embodiments, the composition of the invention is characterized by comprising a hydrocarbon component, which may have characteristics that when used in the amounts disclosed herein impart or enhance one or more of the functions associated with the conditioning agent and/or hydrocarbon compounds described herein to the composition (e.g., spreadability of the composition on the skin, formation and/or stabilization of spheres, or both). In embodiments the hydrocarbon component accounts for between about 20-95 wt. % of the oil phase, but more typically will account for about 40-90 wt. % of the oil phase, about 45-85 wt. % of the oil phase, such as about 50-80 wt. % of the oil phase. Exemplary embodiments include compositions in which the hydrocarbon component makes up about 50 wt. %, about 60 wt. %, about 65 wt. %, about 70 wt. %, about 75 wt. %, about 80 wt. % of the oil phase, or about 85 or about 90 wt. % of the oil phase. In some embodiments, the hydrocarbon component comprises one or more branched hydrocarbons (and may be predominately composed of such branched hydrocarbons, or at least about 90%, at least about 95%, at least about 97%, at least about 98%, or at least about 99% composed of branched hydrocarbons, if not entirely or about 100% composed of branched hydrocarbons), the one or more branched hydrocarbon(s) have one or more side chains. In some embodiments, the sidechains of the branched hydrocarbons are between 1-4 carbons in length.

In other embodiments, the hydrocarbon component is a mixture of hydrolyzed, reduced, or hydrolyzed and reduced natural fatty acids. In some embodiments, the hydrocarbon component is composed of coconut alkanes.

In other embodiments, the anhydrous phase also or alternatively comprises a silicone emollient that is composed of at least one of dimethicone, a dimethicone crosspolymer, cyclopentasiloxane, a cyclopentasiloxane blend, cyclohexasiloxane, cyclotetrasiloxane, cycloheptasiloxane, and phenyl trimethicone. In other embodiments, the at least one of cyclopentasiloxane, cyclohexasiloxane, cyclotetrasiloxane, and cycloheptasiloxane comprises between about 10% to about 100% of the anhydrous phase (e.g., about 15-85 wt. %, such as about 20-100 wt. %, or about 25-100 wt. % of the oil phase).

In other embodiments, the spheres formed in the second state have a diameter of approximately 0.5 to approximately 5 mm (e.g., about 0.75-4.5 mm, such as about 1-5 mm or about 1-4 mm). These values can describe either the range of spheres in the composition, the range of sizes of most of the spheres (e.g., at least about 75%, at least about 90%, or at least about 95%) or the median and/or mode of the sphere sizes of spheres in the composition. In more particular embodiments the spheres have an average diameter of 0.75-3.5 mm or an average diameter of about 1-4 mm, 1.5-3 mm, or 1.25-3.75 mm (e.g., about 0.5 mm, about 1 mm, about 1.5 mm, about 2 mm, about 2.5 mm, about 3 mm, about 3.5 mm, about 4 mm, or about 5 mm).

In other embodiments, most if not all of the spheres in the second state are maintained (stay formed) (or are "stable") for a period of at least 30 minutes from when they are formed, typically through agitation (e.g., through manual agitation) of the composition. In other embodiments, a majority or all of the spheres stay formed for at least 1 hour. In other embodiments, the spheres stay formed for at least 2 hours. In other embodiments, the spheres stay formed for at least 8 hours. In still other embodiments a majority of the spheres, an even greater percentage (e.g., at least about ⅔rds of the spheres, at least about 75% of the spheres, at least about 90% of the spheres), or essentially all of the spheres (about 100%) remain stable for a period of at least one day, at least 2 days, at least one week, at least three weeks, or at least one month. In other embodiments, a similar amount of the spheres stay formed for at least 2, at least 4, or even at least 6 months, with no further requirement for agitation. In other embodiments, the spheres stay formed for at least 1 year. In other embodiments, the spheres stay formed for at least 2 years. In other embodiments, the spheres stay formed for at least 3 years. In other embodiments, the spheres stay formed for at least 42 months.

In some embodiments, the disclosed sphere forming composition is configured for carrying keratin materials, in particular for administration to the skin. In some embodiments, the disclosed composition is surfactant free and is configured for easy application on the skin. The disclosed composition can have good cosmetic properties, particularly in terms of texture. In some embodiments, the disclose composition is kinetically stable, (e.g. room temperature, or a high temperature such as 50° C.). In some examples, the disclosed composition is configured to suspend oils in an aqueous gel and avoids the need for any added surfactants. This can result in no added residue on the skin (as can be determined through, e.g., objective tests known in the art and/or through subjective evaluation in a user trial of the product).

In some embodiments, the composition described herein may be used for skin conditioning or hair conditioning, the composition described herein, having good cosmetic properties in terms of visual appearance, texture, skin absorption rates, and ability to incorporate additional actives and ingredients (e.g. retinol, vitamin C), which, as noted elsewhere herein, can be considered "functional components". Additional examples of such "functional components" are described elsewhere herein.

BRIEF DESCRIPTION OF THE DRAWINGS

Various embodiments are depicted in the accompanying drawings for illustrative purposes. The drawings should not be interpreted as limiting the scope of this disclosure. Various features of different disclosed embodiments can be combined to form additional embodiments, which are part of this disclosure. Any one feature, or any combination of features, of any embodiment can be included in any other embodiment.

DETAILED DESCRIPTION

Overview

Figure 1:
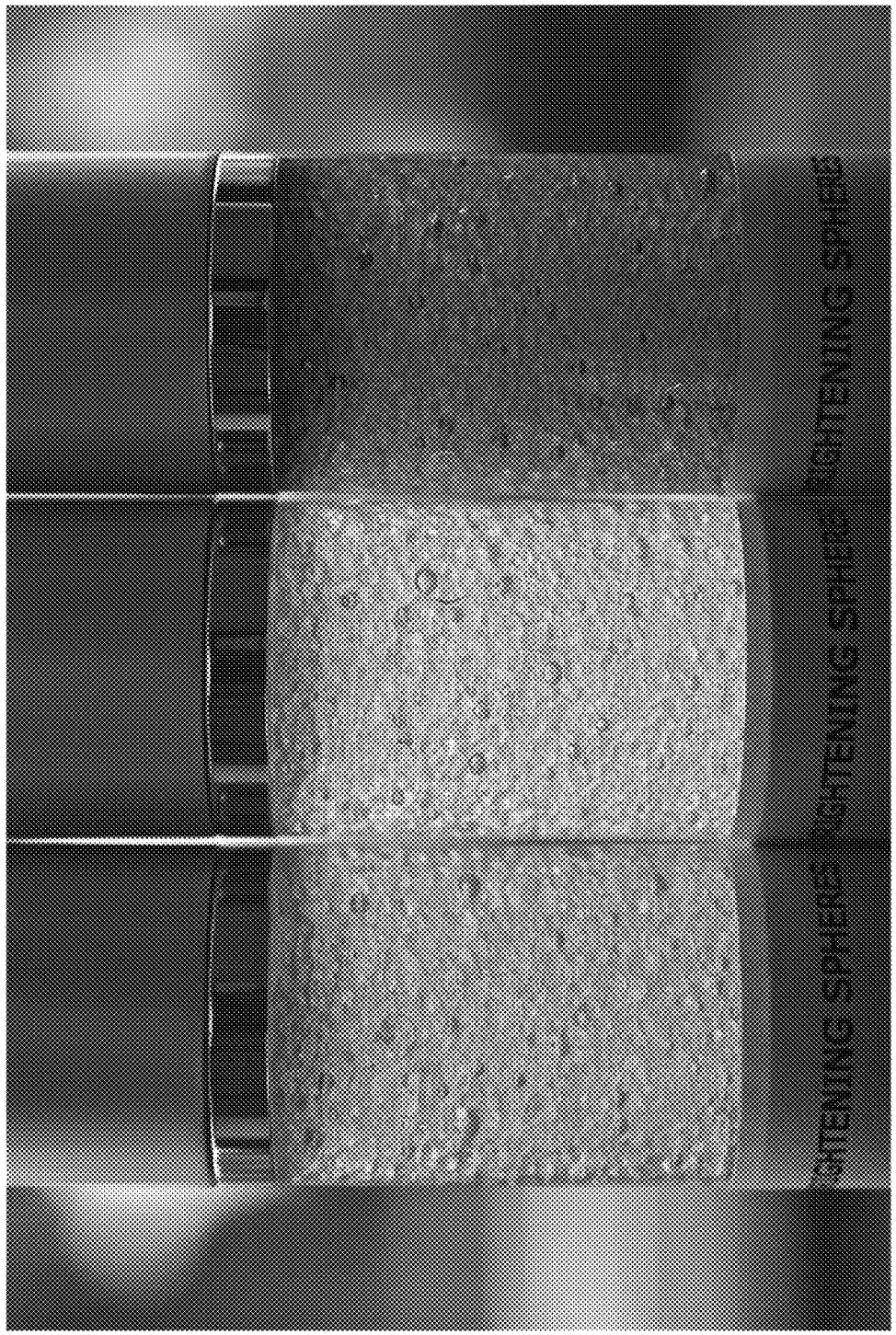
FIG. 1 illustrates three non-limiting embodiments of a sphere forming composition according to several embodiments disclosed herein comprising a 75% water phase and a 25% anhydrous phase resulting in formation of spheres ranging between 2 mm to 4 mm. Each of the three compositions differs in the color ingredient it contains.

Many cosmetic products involve active ingredients that can be either water-soluble or oil-soluble. In order for such products to be formulated, these normally immiscible liquids need to be intermixed to ensure the active ingredients are evenly distributed throughout the product. Existing solutions to intermix immiscible liquids, such as oil/silicone and water, involve the use of emulsifiers or solubilizers (e.g. Carbomer, Cetearyl alcohol, Emulsifying Wax-NF, Lecithin, PEG-20 Stearate, Propylene Glycol, Polysorbate 20, or PEG 40 Hydrogenated Castor Oil). However, as noted above, emulsifiers can be sticky and create products with an undesirable tacky feel. Thus, typically compositions provided by the invention will lack such components. The functionality of the compositions of the invention without such components is a surprising property of compositions according to certain embodiments of the invention. Exceptions to this guidance may exist where other properties of a composition, such as a mixture of chemical species of a desired component, results in the presence of some amount of such compositions being acceptable. For example, where the composition of the invention includes an ester emollient, such as some MIGLYOL-type ester emollients (e.g., MIGLYOL PPG 810), the composition may comprise some amount of propylene glycol. The amounts of such components will typically be limited to less than about 20 wt. % of the composition and more typically to less than about 10 wt. %, less than about 7.5 wt. %, less than about 5 wt. %, less than about 2.5 wt. %, less than about 1 wt. %, less than about 0.5 wt. %, or even less than about 0.1 wt. % of the composition.

Other existing solutions include creating "beads" or "shells" that encapsulate one liquid within another. However, the creation of "beads" requires encapsulation materials that can be hard to break and leave residue where applied. Accordingly, encapsulating agents and agents that have similar functions, such as film-forming emulsifiers and/or film-forming polymers are typically absent from the compositions of the present invention, reflecting a surprising aspect of the invention.

According to several embodiments, disclosed is a composition that begins as a multi-phase structure including a plurality of immiscible liquids that, upon discrete agitation, suspends one of the plurality of liquids into discrete shapes (e.g., in spheres or bubbles—such shapes being referred to as "spheres" herein as described further below). In some embodiments, the composition includes a water phase and an anhydrous (for example, oil or silicone or ester) phase. As will be discussed in more detail below, a thickener can be added to the water phase to assist in producing sphere portions from the oil phase of the composition.

As used herein, the term "spheres" shall be given its ordinary meaning and shall also refer to generally spherical or spheroid shapes with an outer surface that encapsulates a second material or phase. Shapes that are globular, ball-shaped, orb-shaped, ovoid or otherwise shaped in which an outer surface defines an interior volume filled, at least in part, by another material shall also fall within the term "sphere".

The agitation applied to mix the two phases and wherein spheres are formed may take place upon initial formulation during manufacturing or also or alternatively may be undertaken by the final product user. Agitation may be automated, as in part of an automated manufacturing process, or manual, e.g. shaken by hand, as in a manual manufacturing process or as conducted by an end product user. The amount of agitation that is sufficient or optimal to form spheres will vary with the particular make-up of the composition, the desired amount of spheres, and other factors. Typically, with reasonable experimentation, optimal agitation conditions can be selected.

The formed spheres are stable and can be configured to last for specific durations depending on modifications to the formula. In some embodiments, the spheres can release back into the multi-phase structure after a specific period of time. For example, by adjusting the ratio of thickener in the water phase and the ratio of oil or silicone or ester to water, the size and duration of the spheres formed can be controlled. This is a single example; others are exemplified elsewhere herein.

As well the formed spheres can be customized in terms of the benefits applied to the skin or hair of the user. In some embodiments, the composition can be optimized depending on the application of the product—for example the composition for a haircare formula may differ from the composition for a skincare formula.

Benefits

It has been discovered that the selection of appropriate gelling agents; silicones or esters; and aqueous-insoluble, synthetic, branched hydrocarbons can result in a formulation having the ability to begin as two separate phases, the two phases being a water phase and an anhydrous phase, and capable of, upon agitation, forming spheres of anhydrous phase suspended in the aqueous phase. Spheres formed are capable of a duration of substantial amounts of time, such as more than 1 month, more than 3 months, more than 6 months, more than 12 months, or even greater than 3 years. The compositions described herein have the ability to carry and often approximately evenly distribute actives and elements (functional components) to the skin, providing beneficial aesthetic or sensorial properties to the composition, without the use of traditional emulsifiers or solubilizers, and further exhibit and/or maintain a preferred duration of spheres, exhibit and/or maintain a preferred absorption rate, exhibit and/or maintain a preferred aesthetic, e.g. texture, feel, tackiness, and/or exhibit and/or maintain a preferred sensorial attribute such as clarity, e.g. as measured by light transmittance. Maintaining a property in this context generally means retaining the property or at least most of the property or a substantially majority of the initial property for at least the same period of time as the majority of spheres are maintained in the composition, or for such a period combined with a period prior to agitation. The various components described above and alternatives thereof described elsewhere herein, such as various gelling agents, silicones or esters, and branched hydrocarbons or esters, included in the composition, are selected and used in amounts such that the composition has preferred characteristics and is capable of being modified according to specific characteristics.

In some embodiments, the formulations disclosed herein can act as a vehicle or a base formulation to which additional ingredients, such as one or more functional components, can be added. The disclosed formulation, in addition to enabling the intermixing of two immiscible liquids, also provides a number of additional benefits.

As previously described, many cosmetic products involve active ingredients that can be either water-soluble or oil-soluble and in order for such products to be formulated, these normally immiscible liquids need to be intermixed to ensure the active ingredients are evenly distributed throughout the product. The inventive composition described herein (which alternatively is also sometimes referred to herein as "the formulation") is able to evenly distribute incorporated actives and other oil- or water-soluble beneficial ingredients without the use of traditional emulsifiers or solubilizers e.g. without the use of carbomer, cetearyl alcohol, emulsifying, lecithin, stearates, polyethylene glycols, or glycol-based preservatives. The inventive compositions described herein do not include a film-forming emulsifier other than the possible use of ester emollients in lieu of or in combination with a silicone which could potentially form a low to medium level film. Additional aspects of the present invention further distinguish it from prior art, such aspects including the composition described herein being free of lipophilic gelling agents, a salt form of a neutralized acid in an amount greater than 0.5 wt. %, polyacrylates, and film-forming agents comprising at least one anionic polymer and at least one cationic polymer.

As previously described, many traditional sphere-based compositions utilize "bead" technology, often also referred to as "shells" which encapsulate one phase, separating it from a second phase. Such shells, often referred to as beads, are commonly composed of cellulose, mannitol, gellan gum, xylitol, lactose, carrageenan, algin/alginate, and/or hydroxypropyl methycellulose. Biodegradable polymers may also be utilized, such as poly-α-esters, polyalkylcyanoacrylates, and polyamidoamine dendrimers. One benefit of the inventive composition described herein is that it does not contain elements which create a physical film or solid barrier around the anhydrous phase when suspended as spheres within the water phase upon agitation which may leave residue on the skin surface when the inventive formulation is utilized in topically applied compositions. While some silicone alternatives embodied herein, such as an ester-based alternative, could potentially create a low to medium level film, the preferred selection would be such that no residue is left on the skin upon application. Such residue may require additional rubbing to instigate the full absorption of the product by the skin or also or alternatively take more time for the skin to absorb. Selected elements in the composition are preferably chosen such that no additional rubbing or alternative force to induce absorption is required. In addition, traditional sphere-based compositions comprise beads or particles often ranging from 30-1500 microns. Spheres formed by the inventive formulation described herein range in average size from 1 mm to 5 mm in diameter.

In some embodiments, the composition produces spheres which are stable, the composition being capable of transmitting a significant amount of light, and is capable of being absorbed quickly by the skin without the requirement of excessive or additional manual rubbing or any other applied force to induce absorption due to the lack of a significant film-forming emulsifier around the spheres which requires additional effort or takes additional time to induce absorption. An ester emollient could potentially contribute a low to medium level film, however such an emollient is selected in preferred formulation so as not to impact the fast absorption rate of the composition described herein.

For example, the composition can have a lightweight serum texture without any detectable residue or film, as may be determined by objective tests known in the art and/or through subjective tests in a population of users. The composition also or alternatively can be characterized as being non-tacky by similar objective measurements of tackiness and/or subjective assessments, usually made by testing the composition in a population of users. As noted above, many cosmetic products include an emulsifier to intermix immiscible liquids such as oil or silicone and water. However, emulsifiers tend to be sticky and can create products with an undesirable tacky feel. Other technologies that create "beads" require encapsulation materials that can leave residue on the skin or hair when broken. Furthermore, because the disclosed does not contain an emulsifier, the oil or silicone or ester phase is captured in larger quantities (e.g. in spheres) when compared to an emulsion. The larger spheres and absence of an emulsifier gives the product a better feel when applied to skin, and reflects a surprising property of the invention.

In some embodiments, the compositions disclosed herein can contain a high percentage of oil or silicone or ester yet will have a low viscosity. By comparison, an emulsified water and oil or silicone or ester formula will generally need to have a high viscosity with a high oil or silicone or ester content. This low viscosity can allow the anhydrous phase (for example, oil or silicone or ester) to better mix with the water phase. In some embodiments, the lower viscosity can allow the formula create larger spheres when the mixture is agitated. The larger spheres can give the agitated composition a better appearance. In some embodiments, the larger spheres can help to make the composition easier to dispense.

Figure 3:
FIG. 3 illustrates an additional embodiment of a sphere forming composition comprising a 65% water phase and a 35% anhydrous phase resulting in formation of spheres ranging between 2 mm to 4 mm. The right vial illustrates the composition after is has been agitated. The left vial illustrates the embodiment of the composition after two (2) hours have elapsed.

The formed spheres according to several embodiments disclosed herein can also be visually distinctive. In some embodiments, coloring can be added into the water phase or the anhydrous (for example, oil or silicone or ester) phase to create an attractive appearance to the composition. Exemplary colorants include but are not limited to black iron oxide, in some embodiments having the trade name Aquaspersabil BIO available from Presperse; and colorizing algae extracts such as Lanablue™, available from Lucas Meyer cosmetics. As noted above, in some embodiments, the size and/or duration (e.g., longevity) of the formed spheres can be controlled by modifications to the formula. In some embodiments, the formed spheres can range from about 0.5 mm to about 5.0 mm in size. In some examples, the size of the formed spheres can be controlled by changes in the ratios of certain ingredients when combined with dimethicone or a dimethicone crosspolymer. In some embodiments, the dimethicone or dimethicone crosspolymer can help to set the size and duration of the formed spheres. In some embodiments, the spheres can remain formed in the composition for an indefinite period of time. In some embodiments, the composition will not separate (and the spheres will remain formed) for up to about 30 minutes, about 1 hour, about 2 hours, about 8 hours, about 6 months, about 1 year, about 2 years, etc. FIG. 3 illustrates a non-limiting example of a composition where the spheres are configured to remain formed for two (2) hours. As shown, the vial on the right illustrates the composition shortly after it has been agitated with formed spheres ranging between 2 mm and 4 mm. The vial on the left illustrates the composition after two (2) hours have elapsed, and the spheres have the opportunity to separate out into the water phase and the anhydrous phase. In some examples, the formed spheres can remain in the composition by increasing a thickener added in the water phase.

The ability to intermix two immiscible liquids—such as water and oil or silicone or ester—enable a greater range of active ingredients to be used in the composition. In some embodiments, the disclosed composition allows formulators to use a greater range of active ingredients because both water soluble and oil or silicone or ester soluble active ingredients can be included. In some examples, active ingredients can be loaded into both the water and oil or silicone or ester phases in high concentrations.

The formation of encapsulated spheres can provide formulators with a vehicle for the easy and economical formulation of compositions. In some embodiments, compounding will not require heat or agitation—processes that can diminish the efficacy of active ingredients. Furthermore, because water-active ingredients stay in the water phase while the oil/silicone/ester-soluble ingredients stay in the anhydrous phase, they are not mixed together or react to each other. As many oil soluble active ingredients are unstable in water or react with the water phase to affect the active ingredient's potency and availability, the disclosed compositions can help to keep active ingredients separated. This can create a delivery system that preserves the full efficacy of the active ingredients in each of the different phases.

In some embodiments, the composition can easily penetrate the skin to optimize skin treatment benefits. For example, the composition can brighten complexion and boost collagen activity for more supple skin, and a renewed appearance and/or feel. In some embodiments, ingredients can include Neurocap, Brightenyl, Niacinamide, SpecWhite® Plus, and copper derivative. In some embodiments, the composition can be configured for use on all skin types—even skin with acne and/or sensitive skins—and can be layered under other topical compositions.

Example Formulations and Exemplary Embodiments

In some embodiments, the multi-phase composition can include a water phase and an anhydrous phase. In some embodiments, the percent of the water phase can range between 5%-90% and the percent of the anhydrous phase can range between 5%-90%. In some embodiments, the ratio between the water phase and the anhydrous phase can be about 10:1, about 5:1, about 2.5:1, about 1:1, about 1:2.5, about 1:5, about 1:10. In some embodiments, the composition can range from a 10% anhydrous phase and a 90% water phase to a 75% anhydrous phase and a 25% water phase.

In some embodiments, the water phase can range, depending on the composition, from clear to a slightly semi-viscous serum. The coloration of the water phase can range from straw to green colored, however any color can be used. In some embodiments, the pH level of the water phase can have a pH that ranges from 3.5-8.0. For example, the water phase can have a pH of about 3.5 to about 3.6, about 3.6 to about 3.7, about 3.7 to about 3.8, about 3.8 to about 3.9, about 3.9 to about 4.0, about 4.0 to about 4.1, about 4.1 to about 4.2, about 4.2 to about 4.3, about 4.3 to about 4.4, about 4.4 to about 4.5, about 4.5 to about 4.6, about 4.6 to about 4.7, about 4.7 to about 4.8, about 4.8 to about 4.9, about 4.9 to about 5.0, about 5.0 to about 5.1, about 5.1 to about 5.2, about 5.2 about 5.3, about 5.3 to about 5.4, about 5.4 to about 5.5, about 5.5 to about 5.6, about 5.6 to about 5.7, about 5.7 to about 5.8, about 5.8 to about 5.9, about 5.9 to about 6.0, about 6.0 to about 6.1, about 6.1 to about 6.2, about 6.2 to about 6.3, about 6.3 to about 6.4, about 6.4 to about 6.5, about 6.5 to about 6.6, about 6.6 to about 6.7 about 6.7 to about 6.8, about 6.8 to about 6.9, about 6.9 to 7.0, about 7.0 to about 7.1, about 7.1 to about 7.2, about 7.2 to about 7.3, about 7.3 to about 7.4, about 7.4 to about 7.5, about 7.5 to about 7.6, about 7.6 to about 7.7, about 7.7 to about 7.8, about 7.9, about 7.9 to about 8, and overlapping ranges thereof.

In some embodiments, the viscosity of the water phase can range between 500-15,000 cps. For example, the water phase can have a viscosity of about 500 cps to about 1,000 cps, about 1,000 cps to about 1,500 cps, about 1,500 cps to about 2,000 cps, about 2,000 cps to about 2,500 cps, about 2,500 cps to about 3,000 cps, about 3,000 cps to about 3,500 cps, about 3,500 cps to about 4,000 cps, about 4,000 cps to about 4,500 cps, about 4,500 cps to about 5,000 cps, about 5,000 cps to about 5,500 cps, about 5,500 cps to about 6,000 cps, about 6,000 cps to about 6,500 cps, about 6,500 cps to about 7,000 cps, about 7,000 cps to about 7,500 cps, about 7,500 cps to about 8,000 cps, about 8,000 cps to about 8,500 cps, about 8,500 cps to about 9,000 cps, about 9,000 cps to about 9,500 cps, about 9,500 cps to about 10,000 cps, about 10,000 cps to about 10,500 cps, about 10,500 cps to about 11,000 cps, about 11,000 cps to about 11,500 cps, about 11,500 cps to about 12,000 cps, about 12,000 cps to about 12,500 cps, about 12,500 cps to about 13,000 cps, about 13,000 cps to about 13,500 cps, about 13,500 cps to about 14,000 cps, about 14,000 cps to about 14,500 cps, about 14,500 cps to about 15,000 cps, and overlapping ranges thereof.

In some embodiments, the anhydrous phase can range, depending on the composition, from clear to a slightly hazy serum. The coloration of the anhydrous phase can range from a straw to a clear color, however any color can be used. In some embodiments, the viscosity of the anhydrous phase can range between 50-10,000 cps. For example, the anhydrous phase can have a viscosity of about 50 cps to about 100 cps, about 100 cps to about 200 cps, about 200 cps to about 300 cps, about 300 cps to about 400 cps, about 400 cps to about 500 cps, about 500 cps to about 1,000 cps, about 1,000 cps to about 1,500 cps, about 1,500 cps to about 2,000 cps, about 2,000 cps to about 2,500 cps, about 2,500 cps to about 3,000 cps, about 3,000 cps to about 3,500 cps, about 3,500 cps to about 4,000 cps, about 4,000 cps to about 4,500 cps, about 4,500 cps to about 5,000 cps, about 5,000 cps to be about 5,500 cps, about 5,500 cps to be about 6,000 cps, about 6,000 cps to about 6,500 cps, about 6,500 cps to about 7,000 cps, about 7,000 cps to about 7,500 cps, about 7,500 cps to about 8,000 cps, about 8,000 cps to about 8,500 cps, about 8,500 cps to about 9,000 cps, about 9,000 cps to about 9,500 cps, about 9,500 cps to about 10,000 cps, and overlapping ranges thereof.

In addition to a sufficient quantity of deionized water, the formulation of the water phase can include any of the following ingredients. In some embodiments, water can compose between 60%-95% of the water phase.

Sclerotium gum is a natural polysaccharide polymer that can act as a rheology modifier and gelling agent. In some embodiments, sclerotium gum can gel the water phase, thereby permitting the anhydrous phase to be suspended within spheres. In some embodiments, the sclerotium gum can aid the formulation of the spheres and help to set their size and duration. Sclerotium gum can be sold under the trade name Amigel and is available from Alban Muller International. In some embodiments, the water phase includes a percentage of sclerotium gum that ranges from about 0.10%-1.50% (e.g., about 0.2-1.4 wt. % (of the water phase), such as about 0.25-1.35%, about 0.2-1.3%, about 0.2-1.4%, about 0.25-1.35%, about 0.25-1.25%, or about 0.275-1.15%). In some embodiments, the percentage of sclerotium gum in the water phase can be about 0.10% to about 0.15%, about 0.15% to about 0.20%, about 0.20% to about 0.25%, about 0.25% to about 0.30%, about 0.30% to about 0.35%, about 0.35% to about 0.40%, about 0.40% to about 0.45%, about 0.45% to about 0.50%, about 0.50% to about 0.55%, about 0.55% to about 0.60%, about 0.60% to about 0.65%, about 0.65% to about 0.70%, about 0.70% to about 0.75%, about 0.75% to about 0.80%, about 0.80% to about 0.85%, about 0.85% to about 0.90%, about 0.90% to about 0.95%, about 0.95% to about 1.00%, about 1.00% to about 1.05%, about 1.05% to about 1.10%, about 1.10% to about 1.15%, about 1.15% to about 1.20%, about 1.20% to about 1.25%, about 1.25% to about 1.30%, about 1.30% to about 1.35%, about 1.35% to about 1.40%, about 1.40% to about 1.45%, about 1.45% to about 1.50%, and overlapping ranges thereof.

The water phase can also include xanthan gum. Xanthan gum is a natural polysaccharide polymer that can act as rheology modifier and gelling agent. In some embodiments, xanthan gum can gel the water phase, thereby permitting the anhydrous phase to be suspended within spheres. In some embodiments, the xanthan gum contributes to the clarity of the composition, such that the composition has a higher percent light transmittance when incorporated along with sclerotium gum than when sclerotium gum is used alone. In some embodiments, the xanthan gum utilized in exemplified formulations has the trade name Keltrol CG-T, available from CP Kelco. In some embodiments, the water phase includes a percentage of xanthan gum that ranges from about 0.05%-2% (e.g., about 0.05-1.5 wt. % of the water phase, such as about 0.075-1.25% or 0.075-1.5%, such as about 0.05-1.25%, e.g., about 0.05-1% or about 0.075-1%, and often about 0.05-0.95%). In some embodiments, the percentage of xanthan gum in the water phase can be about 0.10% to about 0.20%, about 0.20% to about 0.30%, about 0.30% to about 0.40%, about 0.40% to about 0.50%, about 0.50% to about 0.60%, about 0.60% to about 0.70%, about 0.70% to about 0.80%, about 0.80% to about 0.90%, about 0.90% to about 1.00%, about 1.00% to about 1.10%, about 1.10% to about 1.20%, about 1.20% to about 1.30%, about 1.30% to about 1.40%, about 1.40% to about 1.50%, about 1.50% to about 1.60%, about 1.60% to about 1.70%, about 1.70% to about 1.80%, about 1.80% to about 1.90%, about 1.90% to about 2.00%, or overlapping ranges thereof.

In some embodiments the composition has a significant translucent quality, in that when placed in front of a light source, a significant amount of light is able to be transmitted through the gelled, sphere-filled composition, providing an aesthetically appealing effect which may be described as looking like a glow, translucence, shine, or reflectance. The mixing of the two phases does not create a significant haze or cloudiness within the composition blocking light transmittance.

In some embodiments, the compositions may be formulated such that they are capable of transmitting light in a range of about 40% to about 95%, for example about 45%, about 50%, about 55%, about 60%, about 65%, 0%, a 70%, about 75%, about 80%, about 85%, about 90%, about 92.5%, or about 95%. Preferred embodiments yield a composition with a light transmittance ranging from approximately 50% to approximately 90%. Though not specifically measured, formulations exemplified in Example 13 are capable of transmitting light in a range estimated to be approximately 50% to approximately 90%. This is comparable to common aloe vera sunburn gel, a clear but colored liquid soap, or hand sanitizer. In some embodiments the composition may have a measure of light transmittance within about 30%, within about 25%, within about 20%, within about 15%, within about 10% of Purell brand hand sanitizer.

Pentylene glycol can be included in the water phase to serve as a skin conditioning agent. Pentylene glycol can improve the moisturizing of skin and enhance the penetration of other ingredients. Glycols have been well established in the art as being capable of increasing the absorption rate of compositions containing them. The Symrise white paper titled, "Aid to Enhance Bioavailability of Actives" exemplifies this established art. Pentylene glycol, alone or in combination with one or more other glycols, may hasten the skin-absorption rate of the composition such that the composition may be absorbed by the skin within seconds with no excessive rubbing and no other force being applied. The composition may be free of any other skin-absorption promoting agents to induce such an effect. Pentylene glycol can be sold under the trade name Hydrolite-5 and is available from Symrise AG. In some embodiments, instead of pentylene glycol, butylene glycol or another water-soluble skin conditioning ingredient can be used. Butylene glycol, alone or in combination with one or more other glycols, may hasten the skin-absorption rate of the composition such that the composition may be absorbed by the skin within seconds with no excessive rubbing and no other force being applied. The composition may be free of any other skin-absorption promoting agents to induce such an effect. In some embodiments, the composition does not include a skin conditioning agent. In some embodiments, the water phase includes a percentage of pentylene glycol that ranges from about 0.5%-6% (e.g., about 0.75-5 wt. % of the water phase, such as about 0.5-4%, about 0.5-3.5%, about 0.5-2.5%, or about 0.75-1.5%). In some embodiments, the percentage of pentylene glycol in the water phase can be about 1.00% to about 1.10%, about 1.10% to about 1.20%, about 1.20% to about 1.30%, about 1.30% to about 1.40%, about 1.40% to about 1.50%, about 1.50% to about 1.60%, about 1.60% to about 1.70%, about 1.70% to about 1.80%, about 1.80% to about 1.90%, about 1.90% to about 2.00%, about 2.00% to about 2.10%, about 2.10% to about 2.20%, about 2.20% to about 2.30%, about 2.30% to about 2.40%, about 2.40% to about 2.50%, about 2.50% to about 2.60%, about 2.60% to about 2.70%, about 2.70% to about 2.80%, about 2.80% to about 2.90%, about 2.90% to about 3.00%, about 3.00% to about 3.10%, about 3.10% to about 3.20%, about 3.20% to about 3.30%, about 3.30% to about 3.40%, about 3.40% to about 3.50%, about 3.50% to about 3.60%, about 3.60% to about 3.70%, about 3.70% to about 3.80%, about 3.80% to about 3.90%, about 3.90% to about 4.00%, about 4.00% to about 4.10%, about 4.10% to about 4.20%, about 4.20% to about 4.30%, about 4.30% to about 4.40%, about 4.40% to about 4.50%, about 4.50% to about 4.60%, about 4.60% to about 4.70%, about 4.70% to about 4.80%, about 4.80% to about 4.90%), about 4.90% to about 5.00%, or overlapping ranges thereof.

In some embodiments, the water phase includes a water-soluble acid. Preferred water-soluble acids are alpha-hydroxy acids, even more preferably, glycolic acid. Glycolic acid is an alpha hydroxyl acid that can aid cell turnover and produce skin lightening. Glycolic acid can be included to break down the spheres and return the product to two separate phases more quickly. Glycolic acid has the capability of increasing the density of the aqueous phase of the composition, contributing to the ability of the composition to be modified such that the density difference between the two phases may be used to help control the duration of spheres formed upon mixing of the two phases. Glycolic acid can be sold under the trade name Glypure L-70 and is available from DuPont USA. In some embodiments, the glycolic acid in the composition can be replaced by any other alpha hydroxyl acid, such as lactic acid, malic acid, citric acid, and tartaric acid. Other water-soluble acids may also be substituted in the inventive composition in place of an alpha-hydroxy acid. In some embodiments, the water phase includes a percentage of glycolic acid that ranges from about 0.10%-20.00% (e.g., about 1-15 wt. %, such as about 2-12 wt. %, e.g., about 5-11.5 wt. %, about 6-11 wt. %, or about 7-10.5 wt. %). In some embodiments, the percentage of glycolic acid in the water phase can be about 0.10% to about 0.5%, about 0.5% to about 1.00%, 1.00% to about 1.50%, about 1.50% to about 2.00%, about 2.00% to about 2.50%, about 2.50% to about 3.00%, about 3.00% to about 3.50%, about 3.50% to about 4.00%, about 4.00% to about 4.50%, about 4.50% to about 5.00%, about 5.00% to about 5.50%, about 5.50% to about 6.00%, about 6.00% to about 6.50%, about 6.50% to about 7.00%, about 7.00% to about 7.50%, about 7.50% to about 8.00%, about 8.00% to about 8.50%, about 8.50% to about 9.00%, about 9.00% to about 9.50%, about 9.50% to about 10.00%, about 10.00% to about 10.50%, about 10.50% to about 11.00%, about 11.00% to about 11.50%, about 11.50% to about 12.00%, about 12.00% to about 12.50%, about 12.50% to about 13.00%, about 13.00% to about 13.50%, about 13.50% to about 14.00%, about 14.00% to about 14.50%, about 14.50% to about 15.00%, about 15.00% to about 15.50%, about 15.50% to about 16.00%, about 16.00% to about 16.50%, about 16.50% to about 17.00%, about 17.00% to about 17.50%, about 17.50% to about 18.00%, about 18.00% to about 18.50%, about 18.50% to about 19.00%, about 19.00% to about 19.50%, about 19.50% to about 20.00%), or overlapping ranges thereof.

In some embodiments, the water phase can include sodium hydroxide. Sodium hydroxide is an inorganic salt that can be used to adjust the pH of the formulation. Sodium hydroxide can be included to neutralize the glycolic acid in the composition. Sodium hydroxide can be sold under the trade name Sodium Hydroxide, Pellets, F and is available from Univar. In some embodiments, aminomethyl propanol can be used in place of sodium hydroxide. In some embodiments, the water phase includes a percentage of sodium hydroxide that ranges from about 0.20%-4.00%. In some embodiments, the percentage of sodium hydroxide in the water phase can be about 0.20% to about 0.30%, about 0.30% to about 0.40%, about 0.40% to about 0.50%, about 0.50% to about 0.60%, about 0.60% to about 0.70%, about 0.70% to about 0.80%, about 0.80% to about 0.90%, about 0.90% to about 1.00%, about 1.00% to about 1.10%, about 1.10% to about 1.20%, about 1.20% to about 1.30%, about 1.30% to about 1.40%, about 1.40% to about 1.50%, about 1.50% to about 1.60%, about 1.60% to about 1.70%, about 1.70% to about 1.80%, about 1.80% to about 1.90%, about 1.90% to about 2.00%, about 2.00% to about 2.10%, about 2.10% to about 2.20%, about 2.20% to about 2.30%, about 2.30% to about 2.40%, about 2.40% to about 2.50%, about 2.50% to about 2.60%, about 2.60% to about 2.70%, about 2.70% to about 2.80%, about 2.80% to about 2.90%, about 2.90% to about 3.00%, about 3.00% to about 3.10%, about 3.10% to about 3.20%, about 3.20% to about 3.30%, about 3.30% to about 3.40%, about 3.40% to about 3.50%, about 3.50% to about 3.60%, about 3.60% to about 3.70%, about 3.70% to about 3.80%, about 3.80% to about 3.90%, about 3.90% to about 4.00%), or overlapping ranges thereof.

The water phase can also include propanediol. Propanediol can be included in the water phase as a solvent or as a preservative. In some embodiments, propanediol can help to prevent or retard microbial growth, and therefore protect the composition—for example when used in a cosmetic product—from spoilage. Propanediol can be sold under the trade name Zemea® and is available from DuPont USA. In some embodiments, the water phase includes a percentage of propanediol from about 1.00%-5.00%. In some embodiments, the percentage of propanediol in the water phase can be about 1.00% to about 1.10%, about 1.10% to about 1.20%, about 1.20% to about 1.30%, about 1.40%, about 1.40% to about 1.50%, about 1.50% to about 1.60%, about 1.60% to about 1.70%, about 1.70% to about 1.80%, about 1.80% to about 1.90%, about 1.90% to about 2.00%, about 2.00% to about 2.10%, about 2.10% to about 2.20%, about 2.20% to about 2.30%, about 2.30% to about 2.40%, about 2.40% to about 2.50%, about 2.50% to about 2.60%, to about 2.60% to about 2.70%, about 2.70% to about 2.80%, about 2.80% to about 2.90%, about 2.90% to about 3.00%, about 3.00% to about 3.10%, about 3.10% to about 3.20%, about 3.20% to about 3.30%, about 3.30% to about 3.40%, about 3.40% to about 3.50%, about 3.50% to about 3.60%, about 3.60% to about 3.70%, about 3.70% to about 3.80%, about 3.80% to about 3.90%, about 3.90% to about 4.00%, about 4.00% to about 4.10%, about 4.10% to about 4.20%, about 4.20% to about 4.30%, about 4.30% to about 4.40%, about 4.40% to about 4.50%, about 4.50% to about 4.60%, about 4.60% to about 4.70%, about 4.70% to about 4.80%, about 4.80% to about 4.90%, about 4.90% to about 5.00%), or overlapping ranges thereof.

In some embodiments, the water phase can also include a water-soluble preservative. The water-soluble preservative can be included as a water-soluble preservative. A water-soluble preservative can avoid the need for a solvent in order to solubilize the preservative in the water phase. In some embodiments, the water-soluble preservative is a sodium benzoate that can be available from Univar. In some embodiments, the water-soluble preservative is a potassium sorbate that can be available from Univar. In some embodiments any water-soluble preservative can be used. In some embodiments, the water-soluble preservative may contain lactic acid, 2-hydroxy-butanedioic acid, citric acid, hydroxy-acetic acid, 2.3-dihydroxy-(2R,3R)-butanedioic acid. In some embodiments, such a preservative has the trade name Argan-O-Cide 7A that is available from Argan. In some embodiments, the water-soluble preservative is composed of water, lactic acid, malic acid, citric acid, glycolic acid, ascorbic acid, tartaric acid, gluconic acid, and propanediol. In some embodiments, the water-soluble preservative has the trade name Geogard Ultra that is available for sale from Lonza Group Ltd. In some embodiments, the water-soluble preservative is composed of sodium benzoate and gluconolactone. In some embodiments, the preservative may contain phenoxyethanol, chlorphenesin, and caprylyl glycol. In some embodiments such a preservative has the trade name Microkill-COS available from Lonza. In some embodiments, the preservative may contain caprylyl glycol, caprylhydroxamic acid, and glycerin. In some embodiments, such a preservative has the trade name Spectrastat, available from Inolex. In some embodiments, the water phase includes a percentage of water-soluble preservative from about 0.20%-1.00%. In some embodiments, the percentage of water-soluble preservatives in the water phase can be about 0.20% to about 0.22%, about 0.22% to about 0.24%, about 0.24% to about 0.26% about 0.26% to about 0.28%, about 0.28% to about 0.30%, about 0.30% to about 0.32%, about 0.32% to about 0.34%, about 0.34% to about 0.36%, about 0.36% to about 0.38%, about 0.38% to about 0.40%, about 0.40% to about 0.42%, about 0.42% to about 0.44%, about 0.44% to about 0.46%, about 0.46% to about 0.48%, about 0.48% to about 0.50%, about 0.50% to about 0.52%, about 0.52% to about 0.54%, about 0.54% to about 0.56%, to about 0.56% to about 0.58%, about 0.58% to about 0.60%, about 0.60% to about 0.62%, about 0.62% to about 0.64%, about 0.64% to about 0.66%, about 0.66% to about 0.68%, about 0.68% to about 0.70%, about 0.70% to about 0.72%, about 0.72% to about 0.74%, about 0.74% to about 0.76%, about 0.76% to about 0.78%, about 0.78% to about 0.80%, about 0.80% to about 0.82%. about 0.82% to about 0.84%, about 0.84% to about 0.86%, about 0.86% to about 0.88%, about 0.88% to about 0.90%, about 0.90% to about 0.92%, about 0.92% to about 0.94%, about 0.94% to about 0.96%, about 0.96% to about 0.98%, about 0.98%) to about 1.00%, or overlapping ranges thereof.

The formulation of the anhydrous phase can and typically will include a hydrocarbon component, which typically and advantageously can be a low viscosity, low density, and/or highly spreadable synthetic hydrocarbon, as such characterizations would be understood in the art. The hydrocarbon component of formulations/compositions of the invention can impart other properties such as detectably modifying the size and duration of the spheres formed when the water and anhydrous phases of the inventive composition are mixed upon agitation. The hydrocarbon component also or alternative can provide emollient properties/functions to the composition. The hydrocarbon component of the invention often will comprise or be composed entirely of branched hydrocarbons (in other cases, the hydrocarbon can be composed of at least about 50%, at least about 75%, or at least about 90% branched hydrocarbons). Such hydrocarbons used in the composition typically will be water-insoluble. Such hydrocarbons may be soluble with other silicones or esters. Exemplary hydrocarbons utilized in this formulation are often C8 to C20 hydrocarbons (i.e., hydrocarbons having a primary backbone of between 8 and 20 carbons), e.g., C10 to C18, such as C12 to C16, or having a carbon backbone comprising 3-9 carbons, more preferably 4-8 carbons, most preferably 5-7 carbons. Exemplary hydrocarbons may have a density ranging from approximately 0.6 g/mL to about 0.9 g/mL (e.g., 0.65-0.85 g/mL or 0.7-0.8/0.85 g/mL or about 0.675 g/mL-0.875 g/mL, such as about 0.7 g/mL, about 0.725 g/mL, about 0.75 g/mL, or about 0.71-0.78 g/mL) at 20 degrees Centigrade.

According to embodiments, most of the hydrocarbons in the hydrocarbon component, at least about ¾ths of the hydrocarbons in the hydrocarbon component, essentially all of the hydrocarbons in the hydrocarbon component, or about 100% of the hydrocarbons in the hydrocarbon component will be suitable branched hydrocarbons having one or more sidechains. In many embodiments the compositions comprise branched hydrocarbons having side chains that are relatively short (e.g., most or all of the side chains being less than about $\frac{1}{5}^{th}$ of the length, less than about $\frac{1}{8}^{th}$ of the length, or even less than about $\frac{1}{10}^{th}$ of the length of the primary hydrocarbon backbone of the compound). According to certain embodiments, most of the sidechains of the branched hydrocarbons, at least about ⅔rds of the side chains, at least about ¾s of the side chains, or at least about 9/10s of the side chains are between 1-4 carbons in length, 1-3 carbons in length, or 1-2 carbons in length. In some embodiments all of the side chains of the branched hydrocarbons in the hydrocarbon component are 1-2 carbons in length or only 1 carbon in length. In some embodiments, the hydrocarbon component is predominantly composed of or essentially (at least about 95%) composed of isododecane, squalane, isohexadecane, or a mixture of any or all thereof. In embodiments the hydrocarbon component is predominately composed of or even more substantially composed of (e.g., at least about 75%, at least about 85%, or at least about 95% composed of) an alkane hydrocarbon (lacking any double bonds in the backbone, or even throughout the entirety of the compound), such as isododecane, squalane, or isohexadecane. The hydrocarbon component also or alternatively can be characterized as being mostly composed of, at least ⅔rds or at least ¾ths composed of, or about 100% composed of a saturated oil. Those of skill in the art will recognize that the hydrocarbon component can be provided by a composition consisting of or at least predominately consisting of (e.g., essentially consisting of by being at least 95% composed of) a desired hydrocarbon, such as isododecane or isohexadecane, though commercially available mixtures may include about 1%, about 2%, about 3%, about 4%, or even about 5% of other chemical species in such mixtures (e.g., Armesil 12C comprises about 2% of C8 and C16 species and about 98% isododecane). The hydrocarbon component also or alternatively be provided by a composition that comprises a mixture of the hydrocarbon and other compositions, such as a silicone emollient (e.g., Botanasil GB-21 comprises about 80-85% isododecane and about 15-20% of a silicone emollient component). Branched hydrocarbons typically will include at least 2, at least 3, at least 4, at least 5 or more side chains; however, in many embodiments the side chains of such branched hydrocarbons will comprise 4 carbons at most (e.g., in some embodiments the side chains of the branched hydrocarbons will be limited to C1-C3 or C1-C2 length chains or as described elsewhere herein and exemplified by the provided specific compositions can be limited to single carbon side "chains" bonded to the compound backbone).

The hydrocarbon component, if present, typically will provide one or more of the functions described in connection with such compounds herein and/or described in connection with the conditioning agents of the invention, including measurable improvements in spreadability of the composition, and will often be characterized by having low viscosities (e.g., less than about 1000 cps, less than about 750 cps, or less than about 500 cps, or any other viscosities described herein or known in the art in connection with exemplary hydrocarbon compounds provided herein) and will also exhibit relatively low densities. A specific set of exemplary low viscosity, low density, highly spreadable synthetic hydrocarbons that are useful in many embodiments of the invention include isododecane and isohexadecane.

In other embodiments the hydrocarbon component will comprise a derivative of one or more fatty acids, typically fatty acids modified through reduction and/or hydrogenation, such as is exemplified by coconut alkanes, which can in certain embodiments be used in combination with or in place of branched hydrocarbons, such as isododecane or squalane. According to embodiments, such alternative and/or additive fatty acid-derivative hydrocarbon component members will also or alternatively provide some of the functional characteristics associated with the hydrocarbon component, such as detectably improved spreadability.

Herein, the term "spreadable" is intended to describe the capability to be applied in an even layer across a surface, e.g. the surface of the skin, hair, or both. Characteristics such as but not limited to viscosity, elasticity, structural character (e.g. rigidity and strength) and rheology are critical to an ingredient or composition's spreadability. As applied to the synthetic hydrocarbons of the present invention, chosen hydrocarbon oils which have a low enough viscosity, alone or in combination with other synthetic hydrocarbons, to be applied as part of the composition evenly to the skin quickly, easily, and without use of excessive effort to ensure that the components of the composition are evenly distributed across the application surface. Those familiar with the art will appreciate the characteristics of high spreadability versus low spreadability; e.g. a highly spreadable synthetic hydrocarbon or composition versus a less spreadable synthetic hydrocarbon or composition.

The formulation of the anhydrous phase can include any of the following ingredients or other suitable ingredients such as those described elsewhere herein. In some embodiments, the anhydrous phase can include isododecane (e.g., as part of or as making up the entirety of the hydrocarbon component and/or the conditioning agent). Isododecane can be included in the anhydrous phase to help maintain the soft, smooth, and pliable appearance of the skin and/or the hair. In some embodiments, when the isododecane is combined with dimethicone or dimethicone crosspolymer, it can help to set the size and the duration the spheres are formed. In some embodiments, isododecane can provide the composition with a lighter feel and better performance when applied to the skin and/or the hair. Isododecane can be sold under the trade name Armesil 12C and is available from Argan. In some embodiments, isohexadecane can be used in place of isododecane. In some embodiments, the anhydrous phase includes a percentage of isododecane from about 5.00%-70.00%. In some embodiments, the percentage of the isododecane in the anhydrous phase can be about 5.00% to about 6.00%, about 6.00% to about 7.00%, about 7.00% to about 8.00%, about 8.00% to about 9.00%, about 9.00% to about 10.00%, about 10.00% to about 11.00%, about 11.00% to about 12.00%, about 12.00% to about 13.00%, about 13.00% to about 14.00%, about 14.00% to about 15.00%, about 15.00% to about 16.00%, about 16.00% to about 17.00%, about 17.00% to about 18.00%, about 18.00 to about 19.00%, about 19.00%, about 19.00% to about 20.00%, about 20.00% to about 21.00%, about 21.00% to about 22.00%, about 22.00% to about 23.00%, about 23.00% to about 24.00%, about 24.00% to about 25.00%, about 25.00% to about 26.00%, about 26.00% to about 27.00%, about 27.00% to about 28.00%, about to 28.00 to about 29.00%, about 29.00% to about 30.00%, about 30.00% to about 31.00%, about 31.00% to about 32.00%, about 32.00% to about 33.00%, about 33.00% to about 34.00%, about 34.00% to about 35.00%, about 35.00% to about 36.00%, about 36.00% to about 37.00%, about 37.00% to about 38.00%, about 38.00% to about 39.00%, about 39.00% to about 40.00%, about 40.00% to about 41.00%, about 41.00% to about 42.00%, about 42.00% to about 43.00%, about 43.00% to about 44.00%, about 44.00% to about 45.00%, about 45.00% to about 46.00%, about 46.00% to about 47.00%, about 47.00% to about 48.00%, about 48.00% to about 49.00%, about 49.00% to about 50.00%, about 50.00% to about 51.00%, about 51.00% to about 52.00%, about 52.00% to about 53.00%, about 53.00% to about 54.00%, about 54.00% to about 55.00%, about 55.00% to about 56.00%, about 56.00% to about 57.00%, about 57.00% to about 58.00%, about 58.00% to about 59.00%, about 59.00% to about 60.00%, about 60.00% to about 61.00%, about 61.00% to about 62.00%, about 62.00% to about 63.00%, about 63.00% to about 64.00%, about 64.00% to about 65.00%, about 65.00% to about 66.00%, about 66.00% to about 67.00%, about 67.00% to about 68.00%, about 68.00% to about 69.00%, about 69.00% to about 70.00%, or overlapping ranges thereof.

The anhydrous phase can also include a combination of isododecane and dimethicone crosspolymer, and in some embodiments the combination is provided by using a mixture of or that comprises such compounds, an example of which is a composition comprising a mixture of isododecane and dimethicone crosspolymer sold under the trade name Botanisil GB-21 which is commercially available from Botanigenics. Botanisil GB-21 can be included in the anhydrous phase to help maintain the soft, smooth, and pliable appearance of skin. In some embodiments, when Botanisil GB-21 is combined with isododecane, it can help to set the size and duration of the formed spheres. In some embodiments, Botanisil GB-21 can be added to provide shine and improve the look and feel of the composition upon application on the skin. In some embodiments, the anhydrous phase can include a percentage of Botanisil GB-21 that ranges from about 5.00%-70.00%). In some embodiments, the percentage of Botanisil GB-21 in the anhydrous phase can be about 5.00% to about 6.00%, about 6.00% to about 7.00%, about 7.00% to about 8.00%, about 8.00% to about 9.00%, about 9.00% to about 10.00%, about 10.00% to about 11.00%, about 11.00% to about 12.00%, about 12.00% to about 13.00%, about 13.00% to about 14.00%, about 14.00% to about 15.00%, about 15.00% to about 16.00%, about 16.00% to about 17.00%, about 17.00% to about 18.00%, about 18.00 to about 19.00%, about 19.00%, about 19.00% to about 20.00%, about 20.00% to about 21.00%, about 21.00% to about 22.00%, about 22.00% to about 23.00%, about 23.00% to about 24.00%, about 24.00% to about 25.00%, about 25.00% to about 26.00%, about 26.00% to about 27.00%, about 27.00% to about 28.00%, about to 28.00 to about 29.00%, about 29.00% to about 30.00%, about 30.00% to about 31.00%, about 31.00% to about 32.00%, about 32.00% to about 33.00%, about 33.00% to about 34.00%, about 34.00% to about 35.00%, about 35.00% to about 36.00%, about 36.00% to about 37.00%, about 37.00% to about 38.00%, about 38.00% to about 39.00%, about 39.00% to about 40.00%, about 40.00% to about 41.00%, about 41.00% to about 42.00%, about 42.00% to about 43.00%, about 43.00% to about 44.00%, about 44.00% to about 45.00%, about 45.00% to about 46.00%, about 46.00% to about 47.00%, about 47.00% to about 48.00%, about 48.00% to about 49.00%, about 49.00% to about 50.00%, about 50.00% to about 51.00%, about 51.00% to about 52.00%, about 52.00% to about 53.00%, about 53.00% to about 54.00%, about 54.00% to about 55.00%, about 55.00% to about 56.00%, about 56.00% to about 57.00%, about 57.00% to about 58.00%, about 58.00% to about 59.00%, about 59.00% to about 60.00%, about 60.00% to about 61.00%, about 61.00% to about 62.00%, about 62.00% to about 63.00%, about 63.00% to about 64.00%, about 64.00% to about 65.00%, about 65.00% to about 66.00%, about 66.00% to about 67.00%, about 67.00% to about 68.00%, about 68.00% to about 69.00%, about 69.00%) to about 70.00%, or overlapping ranges thereof.

The compositions of the invention will typically comprise a silicone emollient component and/or other silicone elements that may lack emollient properties. Compositions having emollient properties are generally known in the art and newly discovered or synthesized compositions can be assessed for emollient properties based on comparison to such known emollients and/or testing for the ability to exhibit emollient functions when applied to a test subject. The silicone emollient can be any suitable silicone composition, examples of which are provided herein. Typically, most, at least about 75%, or at least about 100%, if not 100% of the components of the silicone emollient will exhibit a density of about 0.6 g/cm3-about 0.9 g/cm3 (e.g., about 0.65-0.875 g/cm3, about 0.675-0.865 g/cm3, about 0.68-about 0.86 g/cm3, about 0.69-about 0.85 g/cm3, or about 0.7-about 0.84 g/cm3, e.g., about 0.7-about 0.8 g/cm3, such as about 0.7, about 0.72, about 0.73, about 0.74, about 0.75, about 0.76, about 0.77, or about 0.78 g/cm3, as further exemplified by ranges such as about 0.71-0.78 g/cm3 and 0.72-0.78 g/cm3). Silicone emollients and other silicone components suitable for use in compositions of the invention can vary widely in viscosity, ranging from, e.g., about 4 cts. to about 600,000 cts, such as about 5 cts to about 500,000 cts.

In some embodiments, the anhydrous phase can also include a combination of dimethicone and dimethicone crosspolymer that is sold under the trade name Botanisil GB-41 and is available from Botanigenics. Botanisil GB-41 can be included in the anhydrous phase to help maintain the soft, smooth, and pliable appearance of skin. In some embodiments, when Botanisil GB-21 is combined with isododecane, it can help to set the size and duration of the formed spheres. In some embodiments, Botanisil GB-21 can be added to provide shine and improve the look and feel of the composition upon application to the skin. In some embodiments, the anhydrous phase can include a percentage of Botanisil GB-41 that ranges from 5.00%-70.00% by weight. In some embodiments, the percentage of Botanisil GB-41 in the anhydrous phase can be about 5.00% to about 6.00%, about 6.00% to about 7.00%, about 7.00% to about 8.00%, about 8.00% to about 9.00%, about 9.00% to about 10.00%, about 10.00% to about 11.00%, about 11.00% to about 12.00%, about 12.00% to about 13.00%, about 13.00% to about 14.00%, about 14.00% to about 15.00%, about 15.00% to about 16.00%, about 16.00% to about 17.00%, about 17.00% to about 18.00%, about 18.00 to about 19.00%, about 19.00%, about 19.00% to about 20.00%, about 20.00% to about 21.00%, about 21.00% to about 22.00%, about 22.00% to about 23.00%, about 23.00% to about 24.00%, about 24.00% to about 25.00%, about 25.00% to about 26.00%, about 26.00% to about 27.00%, about 27.00% to about 28.00%, about to 28.00 to about 29.00%, about 29.00% to about 30.00%, about 30.00% to about 31.00%, about 31.00% to about 32.00%, about 32.00% to about 33.00%, about 33.00% to about 34.00%, about 34.00% to about 35.00%, about 35.00% to about 36.00%, about 36.00% to about 37.00%, about 37.00% to about 38.00%, about 38.00% to about 39.00%, about 39.00% to about 40.00%, about 40.00% to about 41.00%, about 41.00% to about 42.00%, about 42.00% to about 43.00%, about 43.00% to about 44.00%, about 44.00% to about 45.00%, about 45.00% to about 46.00%, about 46.00% to about 47.00%, about 47.00% to about 48.00%, about 48.00% to about 49.00%, about 49.00% to about 50.00%, about 50.00% to about 51.00%, about 51.00% to about 52.00%, about 52.00% to about 53.00%, about 53.00% to about 54.00%, about 54.00% to about 55.00%, about 55.00% to about 56.00%, about 56.00% to about 57.00%, about 57.00% to about 58.00%, about 58.00% to about 59.00%, about 59.00% to about 60.00%, about 60.00% to about 61.00%, about 61.00% to about 62.00%, about 62.00% to about 63.00%, about 63.00% to about 64.00%, about 64.00% to about 65.00%, about 65.00% to about 66.00%, about 66.00% to about 67.00%, about 67.00% to about 68.00%, about 68.00% to about 69.00%, about 69.00% to about 70.00% by weight, or overlapping ranges thereof.

In some embodiments, the anhydrous phase can include a silicone component, often making up some, most, or all of the emollient component. Preferred silicones for use in the compositions/formulations of the invention are siloxanes and silanes. In some embodiments, silicone is the sole conditioning agent and/or sole component of the emollient component in the anhydrous phase. In some embodiments, an ester emollient may be substituted for the silicone element of the composition (e.g., a MIGLYOL T-C7, MIGLYOL 8810, or MIGLYOL Coco 810 emollient). In some embodiments, an ester emollient may be utilized alone or in combination with a silicone. Other examples of ester emollients include Jojoba ester emollients or hydrolyzed jojoba esters and/or Jojoba oil, myristyl myristate, isopropyl palmitate, dipentaerythrityl hexacaprylate/hexacaprate, acetylated lanolin alcohol, castor isostearate succinate, cetyl palmitate and other cetyl esters, diethylhexyl carbonate, diisopropyl dimer dilinoleate, isopropyl isostearate, glyceryl esters (e.g., methylsilanol PEG-7 glyceryl cocoate), lauryl laurate, caprylyl caprylate/caprate, ethylhexyl olivate, and glyceryl behenate. With respect to this component and other components of the inventive formulations provided herein, such components can be described as a "means" such that the skilled artisan will recognize that the component is to those compositions described specifically herein as well as their many equivalents known in the art. Thus, for example, in one aspect the invention provides compositions comprising an ester means for emolliency (softening and/or smoothing the skin), which will be interpreted as meaning any of the ester emollients described herein as their equivalents in the art. The same principle of employing a "means" for achieving certain functionalities described herein with respect to the various components of the inventive formulations can be applied to the hydrocarbon component, functional component, and/or preservative components, for example, provided herein. In some embodiments, the anhydrous phase can also include a dimethicone. The dimethicone can act as a moisturizer and skin barrier to hydrate and protect the skin against moisture loss. In some embodiments, dimethicone can be used to help set the size and the duration of the spheres formed. Dimethicone can, in some embodiments protect and moisturize the skin and act as a skin conditioning agent. In some embodiments, the dimethicone can be sold under trade names such as Xiameter PMX-200 Silicone Fluid 50CS, Xiameter PMX-200 Silicone Fluid 100CS, and Xiameter PMX-200 Silicone Fluid 350 CS and is available from Dow Corning. In some embodiments, the anhydrous phase can include a percentage of dimethicone that ranges from about 10.00%-100.00%). In some embodiments, the percentage of dimethicone in the anhydrous phase can be about 10.00% to about 12.00%, about 12.00% to about 14.00%, about 14.00% to about 16.00%, about 16.00% to about 18.00%, about 18.00% to about 20.00%, about 20.00% to about 22.00%, about 22.00% to about 24.00%, about 24.00% to about 26.00%, about 26.00% to about 28.00%, about 28.00% to about 30.00%, about 30.00% to about 32.00%, about 32.00% to about 34.00%, about 34.00% to about 36.00%, about 36.00% to about 38.00%, about 38.00% to about 40.00%, about 40.00% to about 42.00%, about 42.00% to about 44.00%, about 44.00% to about 46.00%, about 46.00% to about 48.00%, about 48.00% to about 50.00%, about 50.00% to about 52.00%, about 52.00% to about 54.00%, about 54.00% to about 56.00%, about 56.00% to about 58.00%, about 58.00% to about 60.00%, about 60.00% to about 62.00%, about 62.00% to about 24.00%, about 64.00% to about 66.00%, about 66.00% to about 68.00%, about 68.00% to about 70.00%, about 70.00% to about 72.00%, about 72.00% to about 74.00%, about 74.00% to about 76.00%, about 76.00% to about 78.00%, about 78.00% to about 80.00%, about 80.00% to about 82.00%, about 82.00% to about 84.00%, about 84.00% to about 86.00%, about 86.00% to about 88.00%, about 88.00% to about 90.00%, about 90.00%, to about 92.00%, about 92.00% to about 94.00%, about 94.00% to about 96.00%, about 96.00% to about 98.00%, about 98.00% to about 100.00%), or overlapping ranges thereof.

The anhydrous phase can also include cyclopentasiloxane. In some embodiments, the cyclopentasiloxane can be included to provide a skin conditioning agent that can impart a soft and silky feel to the skin. In some embodiments, when cyclopentasiloxane is combined with dimethicone or dimethicone crosspolymer, it can help to set the size and duration of the formed spheres. In some embodiments, the cyclopentasiloxane can be sold under the trade name Xiameter PMX-0245 Cyclopentasiloxane and is available from Dow Corning. In some embodiments, cyclohexasiloxane, cyclotetrasiloxane, or cycloheptasiloxane can also be used. In some embodiments, the anhydrous phase can include a percentage of cyclopentasiloxane that ranges from about 10.00%-100.00% by weight. In some embodiments, the percentage of cyclopentasiloxane in the anhydrous phase can be about 10.00% to about 12.00%, about 12.00% to about 14.00%, about 14.00% to about 16.00%, about 16.00% to about 18.00%, about 18.00% to about 20.00%, about 20.00% to about 22.00%, about 22.00% to about 24.00%, about 24.00% to about 26.00%, about 26.00% to about 28.00%, about 28.00% to about 30.00%, about 30.00% to about 32.00%, about 32.00% to about 34.00%, about 34.00% to about 36.00%, about 36.00% to about 38.00%, about 38.00% to about 40.00%, about 40.00% to about 42.00%, about 42.00% to about 44.00%, about 44.00% to about 46.00%, about 46.00% to about 48.00%, about 48.00% to about 50.00%, about 50.00% to about 52.00%, about 52.00% to about 54.00%, about 54.00% to about 56.00%, about 56.00% to about 58.00%, about 58.00% to about 60.00%, about 60.00% to about 62.00%, about 62.00% to about 24.00%, about 64.00% to about 66.00%, about 66.00% to about 68.00%, about 68.00% to about 70.00%, about 70.00% to about 72.00%, about 72.00% to about 74.00%, about 74.00% to about 76.00%, about 76.00% to about 78.00%, about 78.00% to about 80.00%, about 80.00% to about 82.00%, about 82.00% to about 84.00%, about 84.00% to about 86.00%, about 86.00% to about 88.00%, about 88.00% to about 90.00%, about 90.00%, to about 92.00%, about 92.00% to about 94.00%, about 94.00% to about 96.00%, about 96.00% to about 98.00%, about 98.00% to about 100.00% by weight, or overlapping ranges thereof.

In some embodiments, the anhydrous phase can include a cyclopentasiloxane blend. The cyclopentasiloxane blend can be included as a skin conditioning agent that can impart a soft and silky feel upon the skin. In some embodiments, when cyclopentasiloxane is combined with dimethicone or dimethicone crosspolymer, the cyclopentasiloxane can serve to set the size and duration of the formation of the spheres. In some embodiments, the cyclopentasiloxane blend is a mixture of cyclopentasiloxane and cyclohexasiloxane. In some embodiments, the cyclopentasiloxane blend can be sold under the trade name Xiameter PMX-0345 Cyclopentasiloxane Blend and is available from Dow Corning. In some embodiments, cyclohexasiloxane, cyclotetrasiloxane, or cycloheptasiloxane can also be used. In some embodiments, the anhydrous phase can include a percentage of cyclopentasiloxane blend that ranges from about 10.00%-100.00% by weight). In some embodiments, the percentage of cyclopentasiloxane blend in the anhydrous phase can be about 10.00% to about 12.00%, about 12.00% to about 14.00%, about 14.00% to about 16.00%, about 16.00% to about 18.00%, about 18.00% to about 20.00%, about 20.00% to about 22.00%, about 22.00% to about 24.00%, about 24.00% to about 26.00%, about 26.00% to about 28.00%, about 28.00% to about 30.00%, about 30.00% to about 32.00%, about 32.00% to about 34.00%, about 34.00% to about 36.00%, about 36.00% to about 38.00%, about 38.00% to about 40.00%, about 40.00% to about 42.00%, about 42.00% to about 44.00%, about 44.00% to about 46.00%, about 46.00% to about 48.00%, about 48.00% to about 50.00%, about 50.00% to about 52.00%, about 52.00% to about 54.00%, about 54.00% to about 56.00%, about 56.00% to about 58.00%, about 58.00% to about 60.00%, about 60.00% to about 62.00%, about 62.00% to about 24.00%, about 64.00% to about 66.00%, about 66.00% to about 68.00%, about 68.00% to about 70.00%, about 70.00% to about 72.00%, about 72.00% to about 74.00%, about 74.00% to about 76.00%, about 76.00% to about 78.00%, about 78.00% to about 80.00%, about 80.00% to about 82.00%, about 82.00% to about 84.00%, about 84.00% to about 86.00%, about 86.00% to about 88.00%, about 88.00% to about 90.00%, about 90.00%, to about 92.00%, about 92.00% to about 94.00%, about 94.00% to about 96.00%, about 96.00% to about 98.00%, about 98.00% to about 100.00% by weight), or overlapping ranges thereof.

The anhydrous phase can also include a phenyl trimethicone. In some embodiments, the phenyl trimethicone can be included as a skin conditioning agent that can impart a soft and silky feel upon the skin. In some embodiments, when phenyl trimethicone is combined with dimethicone or dimethicone crosspolymer, it can serve to set the size or duration of the spheres formed. In some embodiments, the phenyl trimethicone can be sold under the trade name Dow Corning 556 Cosmetic Grade Fluid. In some embodiments, the anhydrous phase can include a percentage of phenyl trimethicone that ranges from about 10.00%-100.00% by weight. In some embodiments, the percentage of phenyl trimethicone in the anhydrous phase can be about 10.00% to about 12.00%, about 12.00% to about 14.00%, about 14.00% to about 16.00%, about 16.00% to about 18.00%, about 18.00% to about 20.00%, about 20.00% to about 22.00%, about 22.00% to about 24.00%, about 24.00% to about 26.00%, about 26.00% to about 28.00%, about 28.00% to about 30.00%, about 30.00% to about 32.00%, about 32.00% to about 34.00%, about 34.00% to about 36.00%, about 36.00% to about 38.00%, about 38.00% to about 40.00%, about 40.00% to about 42.00%, about 42.00% to about 44.00%, about 44.00% to about 46.00%, about 46.00% to about 48.00%, about 48.00% to about 50.00%, about 50.00% to about 52.00%, about 52.00% to about 54.00%, about 54.00% to about 56.00%, about 56.00% to about 58.00%, about 58.00% to about 60.00%, about 60.00% to about 62.00%, about 62.00% to about 24.00%, about 64.00% to about 66.00%, about 66.00% to about 68.00%, about 68.00% to about 70.00%, about 70.00% to about 72.00%, about 72.00% to about 74.00%, about 74.00% to about 76.00%, about 76.00% to about 78.00%, about 78.00% to about 80.00%, about 80.00% to about 82.00%, about 82.00% to about 84.00%, about 84.00% to about 86.00%, about 86.00% to about 88.00%, about 88.00% to about 90.00%, about 90.00%, to about 92.00%, about 92.00% to about 94.00%, about 94.00% to about 96.00%, about 96.00% to about 98.00%, about 98.00% to about 100.00% by weight), or overlapping ranges thereof.

Although many of the components of the invention are described herein

In embodiments in which a silicone emollient component and a hydrocarbon component are both present, the silicone emollient component typically will account for at least about 5 wt. % of the oil phase, such as at least about 6 wt. % of the oil phase, or at least about 7 wt. % of the oil phase. In such embodiments, the silicone emollient component may often make up about 5-20 wt. % or 4-20 wt. % of the oil phase, such as about 5-15 wt. % or 4-14 wt. % of the oil phase, e.g., about 5-12.5 wt. % of the oil phase.

In certain embodiments of the invention, little or no hydrocarbon component is used in the invention and the oil phase is at least about 75%, at least about 80%, at least about 85%, at least about 90%, at least about 95%, or even about 100% composed of one or more, typically at least two, silicone emollients or a silicone emollient and other silicone element, such as a silicone oil. As exemplified in the Examples, below, in some embodiments a silicone emollient or silicone element component can result in the stable formation of spheres upon agitation having one or more of the desired characteristics of the composition (e.g., the ability to stably incorporate one or more functional ingredients, relative or objectively measured translucence, spreadability, and the ability to retain spheres in the second state after agitation for desired period of time such as at least 1 day, at least 1 week, at least 1 month, etc.).

In some embodiments, the composition may contain an ester in place of one or more described silicone oils. Ester emollients with low molecular weights have the ability to spread quickly, much like embodied silicone oils described herein. In addition, the use of ester emollients beneficially does not affect the desired aesthetic attributes imparted by silicone oils, such as the luxurious skin feel and lack of tackiness. They are often of neutral odor and colorless, therefore do not impact preferred sensorial aspects of the preferred compositions. Non-exclusive examples of ester emollients which may be substituted in place of silicones described herein include coco-caprylate/caprate, triheptanoin, butylene glycol dicaprylate/dicaprate, propylene glycol dicaprylate/dicaprate, neopentyl glycol diheptoate (and) isododecane, neopentyl glycol diheptanoate (and) isododecane, PPG-3 benzyl ether ethylhexanoate, PPG-3 benzyl ether myristate, and PPG-3 isostearyl methyl ether. Other ester emollients are described elsewhere herein. In certain cases, characteristics of the composition, such as being free from polyethylene glycol and/or stearates may render some of the described ester emollients provided herein unsuitable for the particular composition in question. Those of skill in the art will understand such limitations and be able to select from the disclosure and from similar compositions known in the art based upon the characteristics/limitations of the composition in question. Additional alternative ester emollients can include natural and sustainable emollients based on combinations of diheptyl succinate and capryloyl glycerin/sebacic acid copolymer in varying ratios, such emollients known to be capable of replacing dimethicones with particularly low viscosities. Other envisioned replacements include a range of hydrocarbons and hydrogenated hydrocarbons, for example but not limited to a combination of isododecane with hydrogenated tetradecenyl/methylpentadecene, tricaprylin, butylene glycol dicaprylate/dicaprate, triheptanoin, and or similar such elements, for example naturally-sourced materials including mixtures of isoamyl laurate and isoamyl cocoate, *Silybum marianum* ethyl ester, coconut alkanes, and the like. Those skilled in the art will recognize additional emollients with the potential ability to substitute silicone oils in the compositions described herein.

In one embodiment the composition comprises coconut alkanes. Coconut alkanes are understood in the art to be the product obtained from reduction and hydrogenation of a mixture of fatty acids derived from *Cocos Nucifera* (Coconut) Oil. It is envisioned that other fatty acids or mixtures of fatty acids that are suitable for use in or as the hydrocarbon component of compositions in embodiments and that are either reduced, hydrogenated, or both reduced and hydrogenated may be suitable as a component of the hydrocarbon component or even composing the entirety of the hydrocarbon component (in place of a branched hydrocarbon component). Often such compositions will be mixtures of a number of chemical species, as is expected to be the case with respect to e.g., coconut alkanes. Such compositions may contain little (e.g., 10% or less, 5% or less, 2.5% or less, 1% or less, 0.5% or less, or even 0.1% or less) or no detectable amount of branched hydrocarbons. However, in some embodiments a hydrocarbon component of the composition can comprise a mixture of a reduced and/or hydrolyzed fatty acid composition, such as coconut alkanes in combination with one or more branched hydrocarbon compositions, such as isododecane and/or isohexadecane.

As discussed above, changing the ingredients of the composition and/or the ratio between the water phase and the anhydrous phase can create a composition that will have different effects on the spheres formed (for example, different sizes of spheres and/or differences in the duration in which they stay formed). For example, FIG. 1 illustrates how, in some embodiments, changing certain ingredients—such as color—will not affect the size of the spheres formed in the composition. For example, the three formulations in FIG. 1 produce a mixture having different colors but still with spheres ranging between 2 mm and 4 mm.

Figure 2:
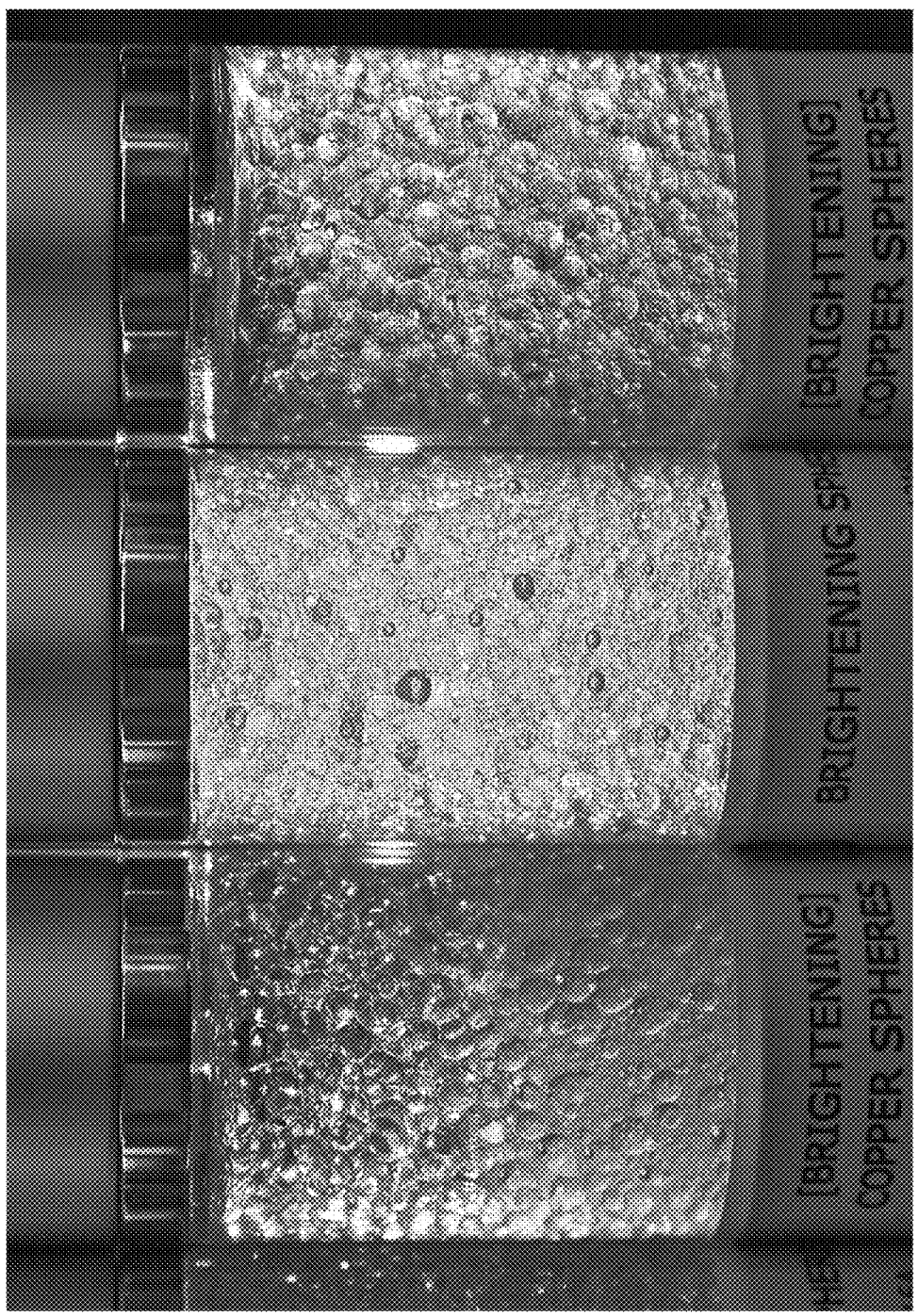
FIG. 2 illustrates three non-limiting embodiments of a sphere forming composition comprising a 65% water phase and a 35% anhydrous phase resulting in formation of spheres ranging between 3 mm to 5 mm. The composition in the leftmost vial separates into two layers after 30 minutes, the composition in the middle vial experiences no separation, and the composition in the rightmost vial separates after two (2) hours.

In some embodiments, the composition can be varied to produce mixtures with spheres that stay formed for different periods of time. For example, as shown in FIG. 2, the compositions of each of the three vials have been varied to produce mixtures that form spheres ranging between 3 mm to 5 mm but that stay formed for 30 minutes (in the leftmost vial), 2 hours (in the rightmost vial), or experience no separation (center vial).

According to certain embodiments, the composition is configured to form spheres when agitated, the composition comprising (a) a water phase comprising between about 25% to about 90% by weight of the composition, the water phase comprising i) water, comprising between about 60% to about 95% by weight; ii) a first gelling agent configured to alter the size and duration of the formed spheres, the first gelling agent comprising sclerotium gum and comprising between about 0.10% to about 1.50% by weight of the water phase; iii) a second gelling agent configured to suspend an anhydrous phase within the water phase, the second gelling agent comprising xanthan gum and comprising between about 0.10% to about 2.00% by weight of the water phase; iv) a skin conditioning agent configured to enhance the penetration of the composition into the skin, the skin conditioning agent comprising at least one of pentylene glycol, butylene glycol, and another water soluble skin conditioning agent and comprising between about 1.00% to about 5.00% of the water phase, and v) a preservative comprising between about 0.20% to about 5.00%; and (b) the anhydrous phase comprising between about 10% to about 75% of the composition, the anhydrous phase comprising a conditioning agent configured to set the size and duration of the formed spheres, the conditioning agent comprising at least one of isododecane, isohexadecane, Botanisil GB-21, and Botanisil GB-41, and comprising between about 5.00% to about 70.00% by weight of the anhydrous phase.

According to some embodiments, the composition may be configured to form spheres when agitated, the composition comprising (a) a water phase comprising between about 25% to about 90% by weight of the composition, the water phase comprising i) water, comprising between about 60% to about 95% by weight; ii) a first gelling agent configured to alter the size and duration of the formed spheres, the first gelling agent comprising sclerotium gum and comprising between about 0.10% to about 1.50% by weight of the water phase; iii) a second gelling agent configured to suspend an anhydrous phase within the water phase, the second gelling agent comprising xanthan gum and comprising between about 0.10% to about 2.00% by weight of the water phase; iv) a skin conditioning agent configured to enhance the penetration of the composition into the skin, the skin conditioning agent comprising at least one of pentylene glycol, butylene glycol, and another water soluble skin conditioning agent and comprising between about 1.00% to about 5.00% of the water phase, and v) a preservative comprising between about 0.20% to about 5.00%; and (b) the anhydrous phase comprising between about 10% to about 75% of the composition, the anhydrous phase comprising a conditioning agent configured to set the size and duration of the formed spheres, the conditioning agent comprising at least one of isododecane, isohexadecane, Botanisil GB-21, and Botanisil GB-41, and comprising between about 5.00% to about 70.00% by weight of the anhydrous phase, and may further comprise (c) a complexion brightener.

According to certain embodiments, the complexion brightener utilized in any described formulation herein may comprise at least one of Neurocap, Brightenyl®, niacinamide, SpecWhite® Plus, copper derivative, or combinations thereof.

According to some embodiments, the composition may be configured to form spheres when agitated, the composition comprising (a) a water phase comprising between about 25% to about 90% by weight of the composition, the water phase comprising i) water, comprising between about 60% to about 95% by weight; ii) a first gelling agent configured to alter the size and duration of the formed spheres, the first gelling agent comprising sclerotium gum and comprising between about 0.10% to about 1.50% by weight of the water phase; iii) a second gelling agent configured to suspend an anhydrous phase within the water phase, the second gelling agent comprising xanthan gum and comprising between about 0.10% to about 2.00% by weight of the water phase; iv) a skin conditioning agent configured to enhance the penetration of the composition into the skin, the skin conditioning agent comprising at least one of pentylene glycol, butylene glycol, and another water soluble skin conditioning agent and comprising between about 1.00% to about 5.00% of the water phase, and v) a preservative comprising between about 0.20% to about 5.00%; and (b) the anhydrous phase comprising between about 10% to about 75% of the composition, the anhydrous phase comprising a conditioning agent configured to set the size and duration of the formed spheres, the conditioning agent comprising at least one of isododecane, isohexadecane, Botanisil GB-21, and Botanisil GB-41, and comprising between about 5.00% to about 70.00% by weight of the anhydrous phase, and may further comprise (c) a water soluble acid such as an alpha hydroxy acid, configured to help break down the spheres formed by the composition.

According to certain embodiments, the water-soluble acid such as an alpha hydroxy acid added to any composition described herein may comprise at least one of glycolic acid or lactic acid and may comprise between about 0.10% to about 20.00% by weight of the water phase.

Some embodiments of the invention described herein, a formulation including glycolic acid may further include an inorganic salt configured to neutralize the water-soluble (e.g. alpha hydroxyl acid such as glycolic acid). According to certain embodiments, the inorganic salt may comprise at least one of sodium hydroxide or aminomethyl propanol and may comprise between about 0.20% to about 4.00% by weight of the water phase.

According to some embodiments, the composition may be configured to form spheres when agitated, the composition comprising (a) a water phase comprising between about 25% to about 90% by weight of the composition, the water phase comprising i) water, comprising between about 60% to about 95% by weight; ii) a first gelling agent configured to alter the size and duration of the formed spheres, the first gelling agent comprising sclerotium gum and comprising between about 0.10% to about 1.50% by weight of the water phase; iii) a second gelling agent configured to suspend an anhydrous phase within the water phase, the second gelling agent comprising xanthan gum and comprising between about 0.10% to about 2.00% by weight of the water phase; iv) a skin conditioning agent configured to enhance the penetration of the composition into the skin, the skin conditioning agent comprising at least one of pentylene glycol, butylene glycol, and another water soluble skin conditioning agent and comprising between about 1.00% to about 5.00% of the water phase, and v) a preservative comprising between about 0.20% to about 5.00%; and (b) the anhydrous phase comprising between about 10% to about 75% of the composition, the anhydrous phase comprising a conditioning agent configured to set the size and duration of the formed spheres, the conditioning agent comprising at least one of isododecane, isohexadecane, Botanisil GB-21, and Botanisil GB-41, and comprising between about 5.00% to about 70.00% by weight of the anhydrous phase, and wherein the preservative incorporated in the formulation comprises propanediol.

According to some embodiments, the composition may be configured to form spheres when agitated, the composition comprising (a) a water phase comprising between about 25% to about 90% by weight of the composition, the water phase comprising i) water, comprising between about 60% to about 95% by weight; ii) a first gelling agent configured to alter the size and duration of the formed spheres, the first gelling agent comprising sclerotium gum and comprising between about 0.10% to about 1.50% by weight of the water phase; iii) a second gelling agent configured to suspend an anhydrous phase within the water phase, the second gelling agent comprising xanthan gum and comprising between about 0.10% to about 2.00% by weight of the water phase; iv) a skin conditioning agent configured to enhance the penetration of the composition into the skin, the skin conditioning agent comprising at least one of pentylene glycol, butylene glycol, and another water soluble skin conditioning agent and comprising between about 1.00% to about 5.00% by weight of the water phase, and v) a preservative comprising between about 0.20% to about 5.00% by weight; and (b) the anhydrous phase comprising between about 10% to about 75% of the composition, the anhydrous phase comprising a conditioning agent configured to set the size and duration of the formed spheres, the conditioning agent comprising at least one of isododecane, isohexadecane, Botanisil GB-21, and Botanisil GB-41, and comprising between about 5.00% to about 70.00% by weight of the anhydrous phase, and wherein the conditioning agent is combined with at least one of dimethicone or a dimethicone crosspolymer or a combination of the two.

According to some embodiments, the composition may be configured to form spheres when agitated, the composition comprising (a) a water phase comprising between about 25% to about 90% by weight of the composition, the water phase comprising i) water, comprising between about 60% to about 95% by weight; ii) a first gelling agent configured to alter the size and duration of the formed spheres, the first gelling agent comprising sclerotium gum and comprising between about 0.10% to about 1.50% by weight of the water phase; iii) a second gelling agent configured to suspend an anhydrous phase within the water phase, the second gelling agent comprising xanthan gum and comprising between about 0.10% to about 2.00% by weight of the water phase; iv) a skin conditioning agent configured to enhance the penetration of the composition into the skin, the skin conditioning agent comprising at least one of pentylene glycol, butylene glycol, and another water soluble skin conditioning agent and comprising between about 1.00% to about 5.00% of the water phase, and v) a preservative comprising between about 0.20% to about 5.00%; and (b) the anhydrous phase comprising between about 10% to about 75% of the composition, the anhydrous phase comprising a conditioning agent configured to set the size and duration of the formed spheres, the conditioning agent comprising at least one of isododecane, isohexadecane, Botanisil GB-21, and Botanisil GB-41, and comprising between about 5.00% to about 70.00% by weight of the anhydrous phase, and wherein the anhydrous phase further comprises at least one of dimethicone, a dimethicone crosspolymer, cyclopentasiloxane, a cyclopentasiloxane blend, cyclohexasiloxane, cyclotetrasiloxane, cycloheptasiloxane, phenyl trimethicone, or a combination thereof.

According to certain embodiments, the use of at least one of cyclopentasiloxane, cyclohexasiloxane, cyclotetrasiloxane, and cycloheptasiloxane comprises between about 10.00% to about 100.00% by weight of the anhydrous phase.

According to some embodiments, the composition may be configured to form spheres when agitated, the composition comprising (a) a water phase comprising between about 25% to about 90% by weight of the composition, the water phase comprising i) water, comprising between about 60% to about 95% by weight; ii) a first gelling agent configured to alter the size and duration of the formed spheres, the first gelling agent comprising sclerotium gum and comprising between about 0.10% to about 1.50% by weight of the water phase; iii) a second gelling agent configured to suspend an anhydrous phase within the water phase, the second gelling agent comprising xanthan gum and comprising between about 0.10% to about 2.00% by weight of the water phase; iv) a skin conditioning agent configured to enhance the penetration of the composition into the skin, the skin conditioning agent comprising at least one of pentylene glycol, butylene glycol, and another water soluble skin conditioning agent and comprising between about 1.00% to about 5.00% by weight of the water phase, and v) a preservative comprising between about 0.20% to about 5.00% by weight; and (b) the anhydrous phase comprising between about 10% to about 75% of the composition, the anhydrous phase comprising a conditioning agent configured to set the size and duration of the formed spheres, the conditioning agent comprising at least one of isododecane, isohexadecane, Botanisil GB-21, and Botanisil GB-41, and comprising between about 5.00% to about 70.00% by weight of the anhydrous phase, and wherein the composition may further include one or more of a complexion brightener, a water soluble acid such as an alpha hydroxyl acid, an inorganic salt, a preservative comprising propanediol, a conditioning agent combined with at least one of dimethicone or a dimethicone crosspolymer, at least one of dimethicone, a dimethicone cross polymer, cyclopentasiloxane, a cyclopentasiloxane blend, cyclohexasiloxane, cyclotetrasiloxane, cycloheptasiloxane, and phenyl trimethicone within the anhydrous phase, which is capable of forming spheres ranging in size from between a diameter of approximately 0.5 mm to a diameter of approximately 5 mm. Such spheres may remain substantially stable for any one of at least 30 minutes, at least 1 hour, at least 2 hours, at least 8 hours, at least 6 hours, at least 1 year, and at least 2 years.

In certain embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. In such a composition, the water can compose between about 60% to about 95% by weight of the water phase, for example about 60%, about 65%, about 70%, about 75%, about 80%, about 85%, about 90%, about 92.5%, or about 95% by weight water.

In certain embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. In such a composition, the anhydrous phase may make up between about 10% to about 75% by weight of the topical application, for example about 20 wt. % to about 50 wt. %, 25% to about 45 wt. %, and in other cases about 30% to about 40% by weight of the topical composition.

In certain embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. In such a composition, the water phase may make up between about 25% to about 90% by weight of the topical composition, for example about 25%, about 30%, about 35%, about 40%, about 45%, about 50%, about 55%, about 60%, about 65%, about 70%, about 75%, about 80%, about 85%, about 87.5%, or about 90% by weight of the topical composition.

In certain embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. In such a composition, the first gelling agent may comprise sclerotium gum in an about between 0.10% to about 1.50% by weight of the water phase. In such a composition, the second gelling agent may comprise xanthan gum in an amount between 0.10% to about 2.00% by weight of the water phase.

In certain embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. In such a composition, the skin conditioning agent may be water soluble and may comprise at least one of pentylene glycol, butylene glycol, and another water-soluble skin conditioning agent, incorporated in an amount ranging from about 1.00% to about 5.00% by weight of the water phase, for example about 1.00%, about 1.50%, about 2.00%, about 2.50%, about 3.00%, about 3.50%, about 4.00%, about 4.50%, about 4.75%, or about 5.00% by weight of the water phase.

In certain embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; (b) an anhydrous phase comprising: i) a conditioning agent configured to set the size and duration of the formed spheres; and (c) a complexion brightener which may comprise at least one of Neurocap, Brightenyl®, niacinamide, SpecWhite® Plus, or copper derivative or a combination thereof.

In certain embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. Such a composition may also include a complexion brightener and such a composition may also include a water-soluble acid configured to help break down the spheres formed by the topical composition. Such a water-soluble acid may be an alpha hydroxyl acid. The alpha hydroxyl acid may comprise at least one of glycolic acid or lactic acid or a combination of the two. Such a water-soluble acid, e.g. alpha hydroxyl acid, may comprise between about 0.10% to about 20.00% by weight of the water phase, for example about 0.1%, about 0.5%, 1.00%, about 2%, about, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight of the water phase.

In some embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. Such a composition may also include a complexion brightener and such a composition may also include a water-soluble acid, e.g. an alpha hydroxy acid such as glycolic acid or lactic acid, configured to help break down the spheres formed by the topical composition. Additionally, the composition may comprise an inorganic salt configured to neutralize the water-soluble acid in the topical composition. Such an organic salt may comprise at least one of sodium hydroxide or aminomethyl propanol or a combination of the two. Such an organic salt may comprise between about 0.2% to about 4.00% by weight of the water phase, for example about 0.2%, about 0.4%, about 0.6%, about 0.8%, about 1%, about 1.2%, about 1.4%, about 1.6%, about 1.8%, about 2.0%, about 2.2%, about 2.4%, about 2.6%, about 2.8%, about 3.0%, about 3.2%. about 3.4%, about 3.6%, about 3.8%, about 3.9%, or about 4.0% by weight of the water phase.

In some embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. Such a composition may optionally include one or more of a complexion brightener, a water-soluble acid, e.g. an alpha hydroxy acid such as glycolic acid or lactic acid, an inorganic salt configured to neutralize the water-soluble acid in the topical composition. In such a composition, the preservative utilized is a water-soluble preservative, and may comprise between about 0.2% and 1.00% by weight of the water phase, for example about 0.2%, about 0.3%, about 0.4%, about 0.5%, about 0.6%, about 0.7%, about 0.8%, about 0.9%, or about 1.00% by weight of the water phase. Such a preservative may comprise propanediol in an amount of about 1.00 to about 5.00% by weight of the water phase, for example about 1.5%, about 2%, about 2.5%, about 3%, about 3.5%, about 4%, about 4.5%, about 4.75%, or about 5% by weight of the water phase.

In some embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. Such a composition may optionally include one or more of a complexion brightener, a water-soluble acid, e.g. an alpha hydroxy acid such as glycolic acid or lactic acid, an inorganic salt configured to neutralize the water-soluble acid in the topical composition. In such a composition, the conditioning agent may comprise at least one of isododecane, isohexadecane, Botanisil GB-21, and Botanisil GB-41. Such conditioning agents may optionally be combined with at least one of dimethicone or a dimethicone crosspolymer. In such compositions, the conditioning agent may comprise between about 5.00% to about 70.00% by weight of the anhydrous phase, for example about 5%, about 10%, about 15%, about 20%, about 25%, 0%, a 30%, about 35%, about 40%, about 45%, about 50%, about 55%, about 60%, about 65%, about 65.7%, or about 70% by weight of the anhydrous phase.

In some embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. Such a composition may optionally include one or more of a complexion brightener, a water-soluble acid, e.g. an alpha hydroxy acid such as glycolic acid or lactic acid, an inorganic salt configured to neutralize the water-soluble acid in the topical composition. In such a composition, the conditioning agent may comprise at least one of isododecane, isohexadecane, Botanisil GB-21, and Botanisil GB-41. Such conditioning agents may optionally be combined with at least one of dimethicone or a dimethicone crosspolymer. Such compositions may include in the anhydrous phase at least one of dimethicone, a dimethicone crosspolymer, cyclopentasiloxane, a cyclopentasiloxane blend, cyclohexasiloxane, cyclotetrasiloxane, cycloheptasiloxane, and phenyl trimethicone. In such a composition, the at least one of cyclopentasiloxane, cyclohexasiloxane, cyclotetrasiloxane, and cycloheptasiloxane comprises between about 10.00% to about 100.00% by weight of the anhydrous phase, for example about 10.00%, about 15.00%, about 20.00%, about 25.00%, about 30.00%, about 35.00%, about 40.00%, about 45.00%, about 50.00%, about 55.00%, about 60.00%, about 65.00%, about 70.00%, about 75.00%, about 80.00%, about 85.00%, about 90.00%, about 95.00%, about 97.50%, or about 100.00% by weight of the anhydrous phase.

In some embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. Such a composition may optionally include one or more of a complexion brightener, a water-soluble acid, e.g. an alpha hydroxy acid such as glycolic acid or lactic acid, an inorganic salt configured to neutralize the water-soluble acid in the topical composition. In such a composition, the conditioning agent may comprise at least one of isododecane, isohexadecane, Botanisil GB-21, and Botanisil GB-41. Such conditioning agents may optionally be combined with at least one of dimethicone or a dimethicone crosspolymer. Such compositions may include in the anhydrous phase at least one of dimethicone, a dimethicone crosspolymer, cyclopentasiloxane, a cyclopentasiloxane blend, cyclohexasiloxane, cyclotetrasiloxane, cycloheptasiloxane, and phenyl trimethicone. Such compositions may form sphere sizes with a diameter approximately 0.5 mm to approximately 5 mm, for example 0.5 mm, approximately 1.0 mm, approximately 1.5 mm, approximately 2.0 mm, approximately 2.5 mm, approximately 3.0 mm, approximately 3.5 mm, approximately 4.0 mm, approximately 4.5 mm, approximately 4.75 mm, or approximately 5 mm in diameter.

In some embodiments, the invention is a topical composition configured to form spheres when agitated, the composition comprising (a) a water phase comprising i) water, ii) a first gelling agent configured to alter the size and duration of the formed spheres, iii) a second gelling agent configured to suspend the anhydrous phase within the water phase, iv) a skin conditioning agent configured to enhance the penetration of the composition into the skin, and v) a preservative; and (b) an anhydrous phase comprising: i) a conditioning agent configured to set the size and duration of the formed spheres. Such a composition may optionally include one or more of a complexion brightener, a water-soluble acid, e.g. an alpha hydroxy acid such as glycolic acid or lactic acid, an inorganic salt configured to neutralize the water-soluble acid in the topical composition. In such a composition, the conditioning agent may comprise at least one of isododecane, isohexadecane, Botanisil GB-21, and Botanisil GB-41. Such conditioning agents may optionally be combined with at least one of dimethicone or a dimethicone crosspolymer. Such compositions may include in the anhydrous phase at least one of dimethicone, a dimethicone crosspolymer, cyclopentasiloxane, a cyclopentasiloxane blend, cyclohexasiloxane, cyclotetrasiloxane, cycloheptasiloxane, and phenyl trimethicone. Such compositions may form sphere sizes with a diameter approximately 0.5 mm to approximately 5 mm. The spheres formed in such compositions may remain formed for at least about 30 minutes, for example at least about 30 minutes, at least about 1 hour, at least about 2 hours, at least about 8 hours, at least about 6 months, at least about 1 year, or at least about 2 years.

One embodiment of the present invention is a composition configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase; and (b) an anhydrous phase comprising between about 10% to about 75% by weight of the composition.

In a particular embodiment of the present invention is a composition configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase; and (b) an anhydrous phase comprising between about 10% to about 75% of the composition. In such a composition, the first gelling agent may comprise sclerotium gum comprising between about 0.10% to about 1.5% by weight of the water phase, for example about 0.10%, about 0.20%, about 0.30%, about 0.40%, about 0.50%, about 0.60%, about 0.70%, about 0.80%, about 0.90%, about 1.00%, about 1.10%, about 1.20%, about 1.30%, about 1.40%, about 1.45%, or about 1.5% by weight of the water phase. In such a composition, the second gelling agent may comprise xanthan gum comprising between about 0.10% to about 2.00% by weight of the water phase, for example about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.45%, or about 1.5% by weight of the water phase.

In a particular embodiment of the present invention is a composition capable of being configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase; and (b) an anhydrous phase comprising between about 10% to about 75% by weight of the composition. In such a composition, the first gelling agent may comprise sclerotium gum comprising between about 0.10% to about 1.5% by weight of the water phase and the second gelling agent may comprise xanthan gum comprising between about 0.10% to about 2.00% by weight of the water phase. In such a composition, the skin conditioning agent may comprise at least one of pentylene glycol, butylene glycol, and another water-soluble skin conditioning agent and comprising between about 1.00% to about 5.00% by weight of the water phase, for example about 1.00%, about 1.50%, about 2.00%, about 2.50%, about 3.00%, about 3.50%, about 4.00%, about 4.50%, about 4.75%, or about 5.00% by weight of the water phase.

In a particular embodiment of the present invention is a composition configured to form and/or capable of forming spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase; and (b) an anhydrous phase comprising between about 10% to about 75% by weight of the composition. In such a composition, the first gelling agent may comprise sclerotium gum comprising between about 0.10% to about 1.5% of the water phase and the second gelling agent may comprise xanthan gum comprising between about 0.10% to about 2.00% by weight of the water phase. In such a composition, the skin conditioning agent may comprise at least one of pentylene glycol, butylene glycol, and another water-soluble skin conditioning agent and comprising between about 1.00% to about 5.00% by weight of the water phase. In such a composition, the anhydrous phase may comprise a conditioning agent configured to set the size and duration of the formed spheres, the conditioning agent comprising at least one of isododecane, isohexadecane, Botanisil GB-21, and Botanisil GB-41, and comprising between about 5.00 to about 70.00% by weight of the anhydrous phase, for example, about 5%, about 10%, about 15%, about 20%, about 25%, about 35%, about 4035%%, about 45%, at 40%, about 45%, about 50%, about 55%, about 60%, about 65%, about 67.5%, or about 70% by weight of the anhydrous phase.

In a particular embodiment of the present invention is a composition capable of forming and/or configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase; and (b) an anhydrous phase comprising between about 10% to about 75% by weight of the composition. In such a composition, the first gelling agent may comprise sclerotium gum comprising between about 0.10% to about 1.5% of the water phase and the second gelling agent may comprise xanthan gum comprising between about 0.10% to about 2.00% of the water phase. In such a composition, the skin conditioning agent may comprise at least one of pentylene glycol, butylene glycol, and another water-soluble skin conditioning agent and comprising between about 1.00% to about 5.00% by weight of the water phase. In such a composition, the anhydrous phase may comprise a conditioning agent configured to set the size and duration of the formed spheres, the conditioning agent comprising at least one of isododecane, isohexadecane, Botanisil GB-21, and Botanisil GB-41, and comprising between about 5.00 to about 70.00% by weight of the anhydrous phase. In such a composition, the water phase may have a pH between about 3.5 to about 8 and a viscosity between about 500 cps to about 15,000 cps, for example a pH of about 3.5, about 4, about 4.5, about 5, about 5.5, about 6, about 6.5, about 7, about 7.5, about 7.75, or about 8, and a viscosity of about 500 cps, about 1000 cps, about 1500 cps, about 2000 cps, about 2500 cps, about 3000 cps, about 3500 cps, about 4000 cps, about 4500 cps, about 5000 cps, about 5500 cps, about 6000 cps, about 6500 cps, about 7000, cps, about 7500 cps, about 8000 cps, about 8500 cps, about 9000 cps, about 9500 cps, about 10,000 cps, about 10,500 cps, about 11,000 cps, about 11,500 cps, about 12,000 cps, about 12,500 cps, about 13,000 cps, about 13,500 cps, about 14,000 cps, about 14,500 cps, about 14,750 cps, or about 15,000 cps.

One embodiment of the present invention is a composition capable of forming and/or configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase; and (b) an anhydrous phase comprising between about 10% to about 75% of the composition. In such a composition, the first gelling agent may comprise sclerotium gum comprising between about 0.10% to about 1.5% by weight of the water phase and the second gelling agent may comprise xanthan gum comprising between about 0.10% to about 2.00% by weight of the water phase. In such a composition, the skin conditioning agent may comprise at least one of pentylene glycol, butylene glycol, and another water-soluble skin conditioning agent and comprising between about 1.00% to about 5.00% by weight of the water phase. In such a composition, the anhydrous phase may comprise a conditioning agent configured to set the size and duration of the formed spheres, the conditioning agent comprising at least one of isododecane, isohexadecane, Botanisil GB-21, and Botanisil GB-41, and comprising between about 5.00 to about 70.00% by weight of the anhydrous phase. In such a composition, the water phase may have a pH between about 3.5 to about 8 and a viscosity between about 500 cps to about 15,000 cps. In such a composition, the anhydrous phase may have a viscosity between about 50 cps to about 10,000 cps, for example about 50 cps, about 150 cps, about 250 cps, about 350 cps, about 450 cps, about 550 cps, about 650 cps, about 750 cps, about 850 cps, about 950 cps, about 1000 cps, about 1100 cps, about 1200 cps, about 1300 cps, about 1400 cps, about 1500 cps, about 1600 cps, about 1700 cps, about 1800 cps, about 1900 cps, about 2000 cps, about 2100 cps, about 2200 cps, about 2300 cps, about 2400 cps, about 2500 cps, about 2600 cps, about 2700 cps, about 2800 cps, about 2900 cps, about 3000 cps, about 3100 cps, about 3200 cps, about 3300 cps, about 3400 cps, about 3500 cps, about 3600 cps, about 3700 cps, about 3800 cps, about 3900 cps, about 4000 cps, about 4100 cps, about 4200 cps, about 4300 cps, about 4400 cps, about 4500 cps, about 4600 cps, about 4700 cps, about 4800 cps, about 4900 cps, about 5000 cps, about 5100 cps, about 5200 cps, about 5300 cps, about 5400 cps, about 5500 cps, about 5600 cps, about 5700 cps, about 5800 cps, about 5900 cps, about 6000 cps, about 6100 cps, about 6200 cps, about 6300 cps, about 6400 cps, about 6500 cps, about 6600 cps, about 6700 cps, about 6800 cps, about 6900 cps, about 7000 cps, about 7100 cps, about 7200 cps, about 7300 cps, about 7400 cps, about 7500 cps, about 7600 cps, about 7700 cps, about 7800 cps, about 7900 cps, about 8000 cps, about 8100 cps, about 8200 cps, about 8300 cps, about 8400 cps, about 8500 cps, about 8600 cps, about 8700 cps, about 8800 cps, about 8900 cps, about 9000 cps, about 9100 cps, about 9200 cps, about 9300 cps, about 9400 cps, about 9500 cps, about 9600 cps, about 9700 cps, about 9800 cps, about 9900 cps, about 9950 cps, or about 10,000 cps.

Compositions that are "configured to" form spheres upon agitation will also be understood as providing support for compositions that are "capable of" forming spheres and/or that simply "form" spheres upon agitation, in accordance with the various exemplary embodiments of the invention provided herein. Accordingly, such phrases are to be understood herein as providing support for each other, regardless of whether there may be differences in meaning that arise from the use of such different phrases to describe the functionality and physiochemical characteristics of the compositions of the invention.

One embodiment of the present invention is a composition configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase, and vi) a complexion brightener; and (b) an anhydrous phase comprising between about 10% to about 75% of the composition. In such a composition, the complexion brightener may comprise at least one of Neurocap, Brightenyl®, niacinamide, SpecWhite® Plus, or copper derivative.

One embodiment of the present invention is a composition configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase, vi) an optional complexion brightener, and vii) a water-soluble acid configured to help break down the spheres formed by the composition; and (b) an anhydrous phase comprising between about 10% to about 75% of the composition. In such a composition, the water-soluble acid may be an alpha hydroxy acid, for example comprising at least one of glycolic acid or lactic acid. Such an acid may comprise between about 0.1% to about 20.00% by weight of the water phase, for example about 0.1%, about 0.5%, about 1.00%, about 2.00%, about 3.00%, about 4.00%, about 5.00%, about 6.00%, about 7.00%, about 8.00%, about 9.00%, about 10.00%, about 11.00%, about 12.00%, about 13.00%, about 14.00%, about 15.00%, about 16.00%, about 17.00%, about 18.00%, about 19.00%, about 19.50%, or about 20.00% by weight of the water phase.

One embodiment of the present invention is a composition configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase, vi) an optional complexion brightener, and vii) a water-soluble acid configured to help break down the spheres formed by the composition, viii) an inorganic salt configured to neutralize the water soluble acid in the composition (e.g. the alpha hydroxy acid such as glycolic acid or lactic acid) and (b) an anhydrous phase comprising between about 10% to about 75% of the composition. In such a composition, the inorganic salt may comprise at least one of sodium hydroxide or aminomethyl propanol and may be present in an amount between 0.20% to about 4.00% by weight of the water phase, for example about 0.2%, about 0.4%, about 0.6%, about 0.8%, about 1.0%, about 1.2%, about 1.4%, about 1.6%, about 1.8%, about 2.0%, about 2.2%, about 2.4%, about 2.6%, about 2.8%, about 3.0%, about 3.2%, about 3.4%, about 3.6%, about 3.8%, about 3.9%, or about 4.0% by weight of the water phase.

One embodiment of the present invention is a composition configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase, vi) an optional complexion brightener, vii) an optional water-soluble acid configured to help break down the spheres formed by the composition, viii) an optional inorganic salt configured to neutralize the water soluble acid in the composition (e.g. the alpha hydroxy acid such as glycolic acid or lactic acid) and (b) an anhydrous phase comprising between about 10% to about 75% by weight of the composition. In such a composition, the preservative may comprise propanediol.

One embodiment of the present invention is a composition configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase, vi) an optional complexion brightener, and vii) an optional water-soluble acid configured to help break down the spheres formed by the composition, viii) an optional inorganic salt configured to neutralize the water soluble acid in the composition (e.g. the alpha hydroxy acid such as glycolic acid or lactic acid) and (b) an anhydrous phase comprising between about 10% to about 75% by weight of the composition. In such a composition, the conditioning agent may be combined with at least one of dimethicone or a dimethicone crosspolymer.

One embodiment of the present invention is a composition configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase, vi) an optional complexion brightener, and vii) an optional water-soluble acid configured to help break down the spheres formed by the composition, viii) an optional inorganic salt configured to neutralize the water soluble acid in the composition (e.g. the alpha hydroxy acid such as glycolic acid or lactic acid) and (b) an anhydrous phase comprising between about 10% to about 75% by weight of the composition. In such a composition, the anhydrous phase may further comprise at least one of dimethicone, a dimethicone crosspolymer, cyclopentasiloxane, a cyclopentasiloxane blend, cyclohexasiloxane, a cyclotetrasiloxane, cycloheptasiloxane, and phenyl trimethicone. In such a composition, the at least one of cyclopentasiloxane, cyclohexasiloxane, cyclotetrasiloxane, and cycloheptasiloxane may comprise between about 10.00% to about 100.00% by weight of the anhydrous phase, for example about 10.00%, about 15.00%, about 20.00%, about 25.00%, about 30.00%, about 35.00%, about 40.00%, about 45.00%, about 50.00%, about 55.00%, about 60.00%, about 65.00%, about 70.00%, about 75.00%, about 80.00%, about 85.00%, about 90.00%, about 95.00%, about 97.50%, or about 100.00% by weight of the anhydrous phase.

One embodiment of the present invention is a composition configured to form spheres when agitated, the composition comprising (a) a water phase comprising between about 25% to about 90% by weight of the composition, the water phase comprising i) water, comprising about 60% to about 95% by weight of the water phase, ii) a first gelling agent configured to alter the size and duration of the formed spheres, iii) a second gelling agent configured to suspend an anhydrous phase within the water phase or also or alternatively contributing to optical clarity of the composition, iv) a skin conditioning agent configured to enhance the penetration of the composition into the skin, and v) a preservative comprising between about 0.20% to about 5.00% by weight of the water phase, vi) an optional complexion brightener, and vii) an optional water-soluble acid configured to help break down the spheres formed by the composition, viii) an optional inorganic salt configured to neutralize the water soluble acid in the composition (e.g. the alpha hydroxy acid such as glycolic acid or lactic acid) and (b) an anhydrous phase comprising between about 10% to about 75% by weight of the composition. In such a composition, the anhydrous phase may further comprise at least one of dimethicone, a dimethicone crosspolymer, cyclopentasiloxane, a cyclopentasiloxane blend, cyclohexasiloxane, a cyclotetrasiloxane, cycloheptasiloxane, and phenyl trimethicone. In such compositions, the spheres formed may have a diameter ranging from between about 0.5 mm to approximately 5 mm, for example 0.5 mm, approximately 1.0 mm, approximately 1.5 mm, approximately 2.0 mm, approximately 2.5 mm, approximately 3.0 mm, approximately 3.5 mm, approximately 4.0 mm, approximately 4.5 mm, approximately 4.75 mm, or approximately 5 mm in diameter. Such spheres may stay formed for at least 30 minutes, for example at least 1 hour, at least 2 hours, at least 8 hours, at least 6 months, at least 1 year, or at least 2 years.

As stated previously, it has been discovered that the selection of appropriate gelling agents; silicones or esters; and aqueous-insoluble, synthetic, branched hydrocarbons can result in a formulation having the ability to begin as two separate phases, the two phases being a water phase and an anhydrous phase, and capable of, upon agitation, forming spheres of anhydrous phase suspended in the aqueous phase. The spheres formed are capable of a duration of greater than 3 years. The compositions described herein have the ability to carry and evenly distribute actives and elements providing beneficial aesthetic or sensorial properties to the composition, without the use of traditional emulsifiers or solubilizers. The gelling agents, silicones or esters, branched hydrocarbons are selected such that the composition has preferred characteristics and is capable of being modified according to specific characteristics. Exemplary modifications may include:

a. If a composition which separates more quickly is desired:
  i. The density difference between the water phase and the anhydrous phase may be targeted, a larger difference in density yielding a composition which tends to separate more quickly than one with a smaller density difference between phases.
  ii. The use of a single gelling agent may be used, as opposed to the use of multiple gelling agents. The preferred single gelling agent is sclerotium gum.
  iii. A lower viscosity silicone or ester oil may be used, as opposed to the use of a higher viscosity silicone oil or ester.
  iv. The use of a glycol may be omitted.
b. If a composition which maintains the duration of spheres formed upon agitation and mixing of the phases is desired:
  i. Multiple gelling agents, most preferably both sclerotium gum and xanthan gum, may be utilized, as opposed to the use of, e.g. sclerotium gum alone.
  ii. A higher viscosity silicone oil or ester may be utilized vs. a lower viscosity silicone oil or ester.
  iii. A glycol may be incorporated into the formulation.
c. If a composition with a higher level of visual clarity is desired:
  i. The use of xanthan as a gelling agent in addition to sclerotium gum may be utilized.
  ii. The use of silicone or ester oil may be utilized as opposed to an alternative oil.
d. If a composition which penetrates the skin more quickly, that is a composition having a higher skin absorption rate, is preferred:
  i. A glycol, preferably pentylene glycol or butylene glycol, may be incorporated.
e. If spheres with a targeted size, e.g. having a diameter within a preferred range is desired:
  i. The viscosity of the individual phases as well as the viscosity of the final formulation may be adjusted via method described herein.
  ii. The silicone or ester oils incorporated may be modified and carefully selected accordingly.
f. If a composition with an increased level of reflectance is desired:
  i. A water-soluble acid, such as an alpha-hydroxy acid, most preferably glycolic acid may be utilized.

According to some embodiments, a beneficial characteristic of the inventive composition is that in some embodiments the formulation is a highly stable composition, receptive to and capable of carrying a variety of water-soluble and oil-soluble actives and functional agents which may contribute to a preferred aesthetic or sensorial experience with the composition. Such agents include but are not limited to colorants, peptides, botanical extracts, retinoids, vitamins, skin whiteners and other ingredients or actives which may impart preferred health or aesthetic characteristics to the composition. Therefore, in addition to the ingredients described as key to the functionality of the inventive composition, the composition may optionally comprise one or more additional functional agents as described, without the need to add an emulsifier or solubilizer, and be capable of maintaining targeted sphere duration as described elsewhere herein.

Typically, the formulations disclosed herein are for cosmetic application to the skin or hair. Accordingly, in many embodiments the compositions can be characterized in lacking any pharmaceutically active ingredients (or lacking any ingredients in an amount that would be considered pharmaceutically active), such as drugs or biologics, especially in any state that would render the composition unsuitable for classification as a cosmetic by the US FDA and similar regulatory agencies. Thus, for example, in one aspect the composition may incorporate a retinoid in an amount that impacts the appearance of the skin, but is not of a type and/or amount that would lead the composition to be classified as a drug by US FDA. The composition also may include inactive compounds, peptides, and the like, which if active may be classified as drugs.

As will be shown below, by varying certain ingredients, the composition can be tailored to specific applications and uses.

EXAMPLES

Below are provided a number of different non-limiting example formulations for the sphere forming compositions of the invention. These examples include actual formulations and test results as well as expected results or properties anticipated to be associated with such formulations based on the principles of the invention, similar results, etc. As none of the examples are critical to the operability of the disclosure, in any portion of any example in which it is unclear whether the disclosure is actual or prophetic the reader may treat the disclosure as prophetic, to avoid any confusion. These examples are intended to illustrate certain aspects and should not be interpreted as limiting the scope of the disclosure.

Example 1

| | Material | A wt % | B wt % | C wt % |
|---|---|---|---|---|
| | Phase 1 (Water Phase) | | | |
| 85° C. | Deionized water | Q.S. | Q.S. | Q.S. |
| Premix @ | Amigel | 0.90 | 0.90 | 0.90 |
| 75° C. | Keltrol CG-T | 0.10 | 0.10 | 0.10 |
| | Hydrolite-5 | 1.00 | 1.00 | 1.00 |
| 40° C. | Glypure L-70 | 8.00 | 8.00 | 8.00 |
| | NaOH @ 20% Solution | 10.00 | 10.00 | 10.00 |
| | Niacinamide PC | 2.00 | 2.00 | 2.00 |
| | Zemea | 1.00 | 1.00 | 1.00 |
| | Sodium Benzoate Powder | 0.50 | 0.50 | 0.50 |
| | FD&C Yellow-5 @ 1% Solution | 0.3125 | 0.60 | — |
| | FD&C Red-40 @ 1% Solution | 0.0438 | 0.21 | — |
| | FD&C Blue-1 @ 1% Solution | — | 0.0225 | — |
| Premix | Aquaspersabil BIO | — | — | 0.0165 |
| | Deionized water | — | — | 1.00 |
| | Phase 2 (Anhydrous Phase) | | | |
| Premix at room temperature | Armesil 12C | 55.00 | 55.00 | 55.00 |
| | Botanisil GB-21 | 45.00 | 45.00 | 45.00 |

In some embodiments, the formulation of Example 1 is a mixture of Phase 1 (water phase) and Phase 2 (anhydrous phase). In some embodiments, the composition is made up of 75 wt. % of Phase 1 and 25 wt. % of Phase 2.

In some examples, the composition of Example 1 can be formed by adding 40% of Phase 1 into a beaker and then slowly mixing Phase 2 into Phase 1 at a rate of 100-200 rpms. The remaining 60% of Phase 1 can then be slowly mixed into the beaker. The composition can then be mixed for a few minutes, or until the two phases are uniform. It is observed that quickly mixing of the Phase 1 and Phase 2 will form smaller spheres.

The produced composition resembles a clear lava lamp and forms a semi-viscous serum. In some embodiments, the composition has a pH of 4.3. In some examples, the viscosity of the water phase is 7680 cps while the viscosity of the finished composition is 6000 cps. In some embodiments, the coloration of formulations A, B, and C is as follows: formulation A is gold champagne, formulation B is light amber, and formulation C is black.

In some embodiments, the spheres formed in Example 1 are between 1-2 mm in diameter. In some examples, the formulation of the composition of Example 1 produces spheres that do not separate into Phase 1 and Phase 2 for at least a period of 2 years.

A stability test was performed for the above disclosed formulation for Example 1. The formulation was observed over a period of three months and the following data was collected:

| | Specifications: |
|---|---|
| Color: | Light straw |
| Odor: | Characteristic |
| Appearance: | Slightly hazy, semi-viscous liquid |
| pH: | N/A |
| Viscosity: | 5,000 cps-10,000 cps |
| Sp. Gr.: | 0.95 (at 25° C.) |
| % Solids: | N/A (weigh 2 g, heat to 130° C.) |

| Initial Stability Readings: | | | | | | |
|---|---|---|---|---|---|---|
| Color | Odor | Appearance | pH | Viscosity (Spindle: 5@10 rpm) | Sp. Gr. | % Solids |
| Light straw | Characteristic | Slightly hazy, semi-viscous liquid | N/A | 6,000 cps | 0.98 | N/A |

| 3 Cycles - Freeze/Thaw: | | | | | |
|---|---|---|---|---|---|
| Cycle | Color | Odor | Appearance | pH | Viscosity |
| 1 | Conforms | Conforms | Conforms | N/A | 6,440 |
| 2 | Conforms | Conforms | Conforms | N/A | 6,360 |
| 3 | Conforms | Conforms | Conforms | N/A | 6,400 |

| | | 1 Week | 1 Month | 2 Months | 3 Months |
|---|---|---|---|---|---|
| | | | Date: | | |
| Temp.: | | (Jan. 19, 2016) | (Feb. 12, 2016) | (Mar. 12, 2016) | (Apr. 12, 2016) |
| 5° C. | Color: | Conforms | Conforms | Conforms | Conforms |
| | Odor: | Conforms | Conforms | Conforms | Conforms |
| | Appearance: | Conforms | Conforms | Conforms | Conforms |
| | pH: | N/A | N/A | N/A | N/A |
| | Viscosity: | 6,120 | 6,720 | 6,400 | 7,000 |
| 25° C. (RT) | Color: | Conforms | Conforms | Conforms | Conforms |
| | Odor: | Conforms | Conforms | Conforms | Conforms |
| | Appearance: | Conforms | Conforms | Conforms | Conforms |
| | pH: | N/A | N/A | N/A | N/A |
| | Viscosity: | 7,080 | 7,840 | 7,440 | 7,840 |
| 40° C. w/75% RH | Color: | Conforms | Conforms | Conforms | Conforms |
| | Odor: | Conforms | Conforms | Conforms | Conforms |
| | Appearance: | Conforms | Conforms | Conforms | Conforms |
| | pH: | N/A | N/A | N/A | N/A |
| | Viscosity: | 7,480 | 8,080 | 7,260 | 8,080 |
| 45° C. | Color: | Conforms | Conforms | Conforms | Conforms |
| | Odor: | Conforms | Conforms | Conforms | Conforms |
| | Appearance: | Conforms | Conforms | Conforms | Conforms |
| | pH: | N/A | N/A | N/A | N/A |
| | Viscosity: | 7,680 | 7,800 | 7,320 | 8,080 |

As illustrated, the composition of Example 1 remains stable over a period of 3 months over a range of different temperatures.

Example 2

| | Material | A wt % | B wt % | C wt % |
|---|---|---|---|---|
| | Phase 1 (Water Phase) | | | |
| Premix | Deionized water | Q.S. | Q.S. | Q.S. |
| | Keltrol CG-T | 0.20 | 0.35 | 0.35 |
| | Emery 917 | 1.00 | 1.00 | 1.00 |
| | Hydrolite-5 | 1.00 | 1.00 | 1.00 |
| | Glypure L-70 | 10.00 | 10.00 | 10.00 |
| | NaOH @ 20% Solution | 12.00 | 12.00 | 12.00 |
| | Niacinamide PC | 1.00 | 2.00 | 2.00 |
| | Whitonyl | 1.00 | 1.00 | 1.00 |
| | Geogard Ultra | 1.00 | 1.00 | 1.00 |
| | Kelate CU | 0.50 | 0.50 | 0.50 |
| | Phase 2 (Anhydrous Phase) | | | |
| | Armesil 12C | 85.00 | 70.00 | 50.00 |
| | Botanisil GB-21 | 15.00 | 30.00 | — |
| | Botanisil GB-41 | — | — | 50.00 |

In some embodiments, the formulation of Example 2 is a mixture of Phase 1 (water phase) and Phase 2 (anhydrous phase). The formulation of the composition of Example 2 can produce a 2-layer semi-viscous serum. The coloration of the composition of Example 2 can be a clear and/or hazy blue. In some embodiments, the composition of Example 2 has a water phase with a pH of 4.05.

In some embodiments, varying the percentage of various ingredients of the composition of Example 2 can results in different formulations that have spheres that form for different periods of time.

For example, formulation A forms a composition with a viscosity of 450 cps. Formulation A, when agitated, forms spheres that begin separating out into the two phases after approximately 3 minutes. Formulation A is observed to separate completely into the two phases after approximately 30 minutes. In some embodiments, formulation A is composed 65 wt. % of the Phase 1 water phase and 35 wt. % of the Phase 2 anhydrous phase. In some examples, the spheres formed in formulation A can range between 3-4 mm in size.

In some examples, formulation B can form a composition with a viscosity of 1400 cps. Formulation B, when agitated, forms spheres that begin separating out into the two phases after approximately 30 minutes. Formulation B is observed to separate completely into the two phases after approximately 1-2 hours. In some embodiments, formulation B is composed 65 wt. % of the Phase 1 water phase and 35 wt. % of the Phase 2 anhydrous phase. In some examples, the spheres formed in formulation B can range between 3-4 mm in size.

In some examples, formulation C can form a composition with a viscosity of 1400 cps. Formulation C, when agitated, forms spheres that begin separating out into the two phases after approximately 2 hours. Formulation C is observed to separate completely into the two phases after approximately 8 hours. In some embodiments, formulation C is composed 65 wt. % of the Phase 1 water phase and 35 wt. % of the Phase 2 anhydrous phase. In some examples, the spheres formed in formulation C can range between 1-2 mm in size.

Example 3

| | Material | wt % |
|---|---|---|
| | Phase 1 (Water Phase) | |
| Premix @ 85° C. | Deionized water | Q.S. |
| | Keltrol CG-T | 0.10 |
| | Emery 917 | 1.00 |
| 40° C. | Amigel | 0.90 |
| | Glypure L-70 | 10.00 |
| | NaOH @ 20% Solution | 12.00 |
| | Niacinamide PC | 2.00 |
| | Geogard Ultra | 1.00 |
| | Hydrolite-5 | 1.00 |
| | FD&C Red-40 @ 1% Solution | 0.07 |
| | FD&C Red-33 @ 1% Solution | 0.093 |
| | Phase 2 (Anhydrous Phase) | |
| Premix @ room temperature | Armesil 12C | 55.00 |
| | Botanisil GB-21 | 45.00 |

In some embodiments, the formulation of Example 3 is a mixture of Phase 1 (water phase) and Phase 2 (anhydrous phase). In some embodiments, the formulation of the composition of Example 3 is formed from a mixture of 75 wt. % of Phase 1 water phase and 25 wt. % of Phase 2 anhydrous phase. In some examples, the composition of Example 3 forms spheres of approximately 1-2 mm in diameter. As well, the spheres formed from the composition of Example 3 is observed to separate into the two phases between 6 months to 1 year after agitation of the composition.

In some examples, the composition of Example 3 forms small spheres in a viscous serum. In some embodiments, the composition can have a light pink color. In some examples, the Phase 1 water phase can have a pH of 4.10.

Example 4

| | Material | D wt % | E wt % | F wt % |
|---|---|---|---|---|
| | Phase 1 (Water Phase) | | | |
| Premix | Deionized water | 70.15 | 70.15 | 70.15 |
| | Keltrol CG-T | 0.35 | 0.35 | 0.35 |
| | Emery 917 | 2.00 | 2.00 | 2.00 |
| | Hydrolite-5 | 1.00 | 1.00 | 1.00 |
| | Glypure L-70 | 10.00 | 10.00 | 10.00 |
| | NaOH @ 20% Solution | 12.00 | 12.00 | 12.00 |
| | Niacinamide PC | 2.00 | 2.00 | 2.00 |
| | Whitonyl | 1.00 | 1.00 | 1.00 |
| | Geogard Ultra | 1.00 | 1.00 | 1.00 |
| | Kelate CU | 0.50 | 0.50 | 0.50 |
| | Phase 2 (Anhydrous Phase) | | | |
| | Botanisil GB-41 | 25.00 | — | — |
| | DC 200, 100 CS | 75.00 | — | — |
| | DC 200, 50 CS | — | 100.00 | — |
| | Chemsil DM-5CS | — | — | 100.00 |

In some embodiments, the formulation of Example 4 is a mixture of Phase 1 (water phase) and Phase 2 (anhydrous phase). In some embodiments, the formulation of the composition of Example 4 produces a 2-layer semi-viscous liquid. The coloration of the composition of Example 4 is a clear blue color. In some embodiments, the composition of Example 4 has a water phase with a pH of 4.0 and a viscosity of 1400 cps.

In some embodiments, varying the percentage of various ingredients of the composition of Example 4 as well as the ratio of the Phase 1 water phase and the Phase 2 anhydrous phase can produce formulations that form spheres for different periods of time.

For example, formulation D forms a composition that, when agitated, forms medium spheres that begin separating out into the two phases after approximately 24 hours. In some embodiments, formulation D is composed 65 wt. % of the Phase 1 water phase and 35 wt. % of the Phase 2 anhydrous phase.

In some examples, formulation E forms a composition that, when agitated, forms spheres that separate slightly after 24 hours. Formulation E is observed to form a top layer of spheres after a period of time between 24-48 hours after agitation. In some embodiments, formulation B is composed 70 wt. % of the Phase 1 water phase and 30 wt. % of the Phase 2 anhydrous phase.

In some examples, formulation E forms a composition that, when agitated, forms medium spheres that begin separating out into the two phases after approximately 24 hours. In some embodiments, formulation E is composed 65 wt. % of the Phase 1 water phase and 35 wt. %) of the Phase 2 anhydrous phase.

Example 5

| | Material | A wt % | B wt % | C wt % |
|---|---|---|---|---|
| | Phase 1 (Water Phase) | | | |
| Premix @ 75° C. | Deionized water | Q.S. | Q.S. | Q.S. |
| | Keltrol CG-T | 0.35 | 0.20 | 0.10 |
| | Emery 917 | 1.00 | 1.00 | 1.00 |
| | Amigel | — | 0.30 | 0.90 |
| | Glypure L-70 | 10.00 | 10.00 | 10.00 |
| | NaOH @ 20% Solution | 12.00 | 12.00 | 12.00 |
| | Niacinamide PC | 2.00 | 2.00 | 2.00 |
| | Geogard Ultra | 1.00 | 1.00 | 1.00 |
| | Kelate CU | 0.50 | 0.50 | 0.50 |
| | Hydrolite-5 | 1.00 | 1.00 | 1.00 |
| | Phase 2 (Anhydrous Phase) | | | |
| | Botanisil GB-41 | 25.00 | 50.00 | — |
| | DC 200,100 CS | 75.00 | — | — |
| | Armesil 12C | — | 50.00 | 55.00 |
| | Botanisil CTB-21 | — | — | 45.00 |

In some embodiments, the formulation of Example 5 is a mixture of Phase 1 (water phase) and Phase 2 (anhydrous phase). In some embodiments, the composition has a ratio of 75 wt. % of Phase 1 and 25 wt. % of Phase 2.

The produced composition forms a 2-layer semi-viscous serum. In some embodiments, the Phase 1 water phase has a pH of 4.0. In some examples, the viscosity can range depending on the composition of the anhydrous phase. For example, the viscosity of formulations A, B, and C can be as follows: 1,400 cps, 2,000 cps, and 5,400 cps. In some examples, the composition can have a coloration that ranges between clear and blue.

Example 6

| | Material | D wt % | E wt % |
|---|---|---|---|
| | Phase 1 (Water Phase) | | |
| 85° C. Premix @ 30° C. | Deionized water | Q.S. | Q.S. |
| | Amigel | 0.50 | — |
| | Keltrol CG-T | 0.20 | 0.35 |
| | Emery 917 | 3.00 | 1.00 |
| 30° C. | Mikrokill COS | 1.00 | — |
| | Geogard Ultra | — | 1.00 |
| | DC 193 | 0.30 | — |
| | Olivatis-15 | 0.50 | — |
| | Niacinamide PC | — | 2.00 |
| | Kelate CU | — | 0.50 |
| | Hydrolite-5 | 5.00 | — |
| | Phase 2 (Anhydrous Phase) | | |
| Premix | Armesil 12C | 70.00 | 70.00 |
| | Botanisil GB-41 | 30.00 | 30.00 |

In some embodiments, the formulation of Example 6 is a mixture of Phase 1 (water phase) and Phase 2 (anhydrous phase). In some embodiments, the composition has a ratio of 65 wt. % of Phase 1 and 35 wt. % of Phase 2.

As discussed above, altering the amount of ingredient in the composition of Example 6 can alter the appearance and separation properties of the formulation. For example, Formulation D forms an opaque 2-layer thick serum when agitated. Formulation D can range in color from clear to slightly hazy. In some embodiments, formulation D can have a pH of 5.6. In some embodiments, formulation D has a viscosity of 4,200 cps.

In contrast, Formulation E forms a 2-layer semi-viscous serum. Formulation E can range in coloration from clear to a light blue color. In some examples Formulation E has a pH of 5.8. In some embodiments, formulation E has a viscosity of 1,500 cps. Formulation E is observed to not completely separate into two layers. Some quantity of the Phase 2 anhydrous phase is observed to remain intermixed with the Phase 1 water phase after the remainder of the formulation has predominantly separated.

Example 7

| | Material | A wt % | B wt % | C wt % |
|---|---|---|---|---|
| | Phase 1 (Water Phase) | | | |
| | Deionized water | Q.S. | Q.S. | Q.S. |
| | Natrosol 250 HHX | 0.40 | 0.40 | 0.40 |
| | Emery 917 | 1.00 | 1.00 | 1.00 |
| | Glypure L-70 | 10.00 | 10.00 | 10.00 |
| | NaOH @ 20% Solution | 12.00 | 12.00 | 12.00 |
| | Kelate CU | 0.40 | 0.40 | — |
| | Geogard Ultra | 1.00 | — | — |
| | Microkill COS | — | 1.00 | — |
| | Spectrastat | — | — | 1.00 |
| | Phase 2 (Anhydrous Phase) | | | |
| Premix | Botanisil GB-41 | 25.00 | 25.00 | 25.00 |
| | DC 200, 100 CS | 75.00 | 75.00 | 75.00 |
| Premix | Armesil 12C | 70.00 | 70.00 | 70.00 |
| | Botanisil GB-21 | 30.00 | 30.00 | 30.00 |

In some embodiments, the formulation of Example 7 is a mixture of Phase 1 (water phase) and Phase 2 (anhydrous phase). In some embodiments, the composition has a ratio of 65 wt. % of Phase 1 and 35 wt. % of Phase 2.

The produced composition forms a 2-layer semi-viscous serum. In some embodiments, the Phase 1 water phase has a pH of 4.0. In some examples, the composition can have a coloration that ranges between clear and light blue.

Formulations A, B, and C have compositions that contain different preservatives. Formulations A, B, and C include the following ingredients respectively: Geogard Ultra, Microkill COS, and Spectrastat. Geogard Ultra is useful as it is water soluble. Microkill COS is observed as producing a slightly hazy composition but is soluble when the two phases are agitated and mixed together.

Example 8

| | Material | D wt % | $D_1$ wt % |
|---|---|---|---|
| | Phase 1 (Water Phase) | | |
| Premix | Deionized water | Q.S. | Q.S. |
| | Keltrol CG-T | 0.35 | 0.35 |
| | Emery 917 | 1.00 | 1.00 |
| | Purac HiPure 90 | 8.00 | 8.00 |
| | NaOH @ 20% Solution | 8.00 | 8.00 |
| | Niacinamide PC | 1.00 | 1.00 |
| | Geogard Ultra | 1.00 | 1.00 |
| | Kelate CU | 0.50 | 0.50 |

-continued

| Material | | D wt % | D₁ wt % |
|---|---|---|---|
| Phase 2 (Anhydrous Phase) | | | |
| Premix | Botanisil GB-41 | 25.00 | — |
| | DC 200, 100 CS | 75.00 | — |
| Premix | Armesil 12C | — | 70.00 |
| | Botanisil GB-21 | — | 30.00 |

In some embodiments, the formulation of Example 8 is a mixture of Phase 1 (water phase) and Phase 2 (anhydrous phase). In some embodiments, the composition has a ratio of 65 wt. % of Phase 1 and 35 wt. % of Phase 2.

The produced composition forms a 2-layer semi-viscous serum. In some embodiments, the Phase 1 water phase has a pH of 4.0. In some examples, the composition can have a coloration that ranges between clear and blue.

Example 8 replaces glycolic acid in the previous formulations with lactic acid in this particular embodiment having the trade name Purac HiPure 90, available from Corbion. Lactic acid can serve the same function as glycolic acid and is observed to not affect the performance of the composition. The mixture formed by formulation D is observed to separate more quickly than formulation D. In some embodiments, the formulations form large spheres when agitated.

Example 9

| | Material | A wt % | B wt % | C wt % |
|---|---|---|---|---|
| | Phase 1 (Water Phase) | | | |
| Q.S. | Deionized water | Q.S. | Q.S. | Q.S. |
| 85° C. | Keltrol CG-T | 0.15 | 0.40 | 0.15 |
| | Emery 917 | 1.00 | 1.00 | 1.00 |
| | Amigel | 0.30 | 0.40 | 0.40 |
| 40° C. | Hydrolite-5 | 1.00 | 1.00 | 1.00 |
| | Glypure L-70 | 10.00 | 10.00 | 10.00 |
| | NaOH @ 20% Solution | 12.00 | 12.00 | 12.00 |
| | Niacinamide PC | 1.00 | 1.00 | 1.00 |
| | Lanablue | 1.00 | 1.00 | 1.00 |
| | Geogard Ultra | 1.00 | 1.00 | 1.00 |
| | Kelate CU | 0.50 | 0.50 | 0.50 |
| | Phase 2 (Anhydrous Phase) | | | |
| | Armesil 12C | 50.00 | 50.00 | 70.00 |
| | Botanisil GB-41 | 50.00 | 50.00 | — |
| | Botanisil GB-21 | — | — | 30.00 |

In some embodiments, the formulation of Example 9 is a mixture of Phase 1 (water phase) and Phase 2 (anhydrous phase). In some embodiments, the composition has a ratio of 70 wt. % of Phase 1 and 30 wt. % of Phase 2.

In some examples, the formulation of the composition of Example 9 produces a 2-layer semi-viscous liquid. The coloration of the composition of Example 9 can range from clear to a light blue color. In some embodiments, the composition of Example 4 has a water phase with a pH of 4.08.

In some embodiments, varying the percentage of various ingredients of the composition of Example 9 can produce formulations that form spheres for different periods of time when the composition is agitated.

For example, formulation A forms a composition that, when agitated, forms medium-large spheres that begin separating out into the two phases after approximately 2 hours. Formulation A is observed to form two separate layers in approximately 24 hours after agitation. Subsequently, formulation A is observed to form a top layer of spheres after approximately 4 days.

In some examples, formulation B forms a composition that, when agitated, forms small-medium spheres that begin separating approximately 2 hours after agitation.

In some examples, formulation C forms a composition that, when agitated, forms medium-large spheres that begin separating out into the two phases after approximately 2 hours. Formulation C is observed to be stable at 4 weeks with a very thin layer of Phase 2 anhydrous phase.

Example 10

| Material | A wt % | B wt % | C wt % | D wt % | E wt % |
|---|---|---|---|---|---|
| Phase 1 (Water Phase) | | | | | |
| Deionized water | Q.S. | Q.S. | Q.S. | Q.S. | Q.S. |
| Keltrol CG-T | 0.35 | 0.20 | 0.20 | 0.35 | 0.20 |
| Emery 917 | 1.00 | 1.00 | 1.00 | 1.00 | 1.00 |
| Hydrolite-5 | 1.00 | 1.00 | 1.00 | 1.00 | 1.00 |
| Glypure L-70 | 10.00 | 10.00 | 10.00 | 10.00 | 10.00 |
| NaOH @ 20% Solution | 12.00 | 12.00 | 12.00 | 12.00 | 12.00 |
| Niacinamide PC | 2.00 | 1.00 | 1.00 | 2.00 | 2.00 |
| Whitonyl | 1.00 | 1.00 | 1.00 | 1.00 | 1.00 |
| Geogard Ultra | 1.00 | 1.00 | 1.00 | 1.00 | 1.00 |
| Kelate CU | 0.50 | 0.50 | 0.50 | 0.50 | 0.50 |
| Phase 2 (Anhydrous Phase) | | | | | |
| Armesil 12C | 70.00 | 70.00 | 85.00 | 50.00 | 50.00 |
| Botanisil GB-21 | 30.00 | 30.00 | 15.00 | — | — |
| Botanisil GB-41 | — | — | — | 50.00 | 50.00 |

In some embodiments, the formulation of Example 10 is a mixture of Phase 1 (water phase) and Phase 2 (anhydrous phase). In some embodiments, the composition has a ratio of 65 wt. % of Phase 1 and 35 wt. % of Phase 2.

In some examples, the formulation of the composition of Example 10 produces a 2-layer semi-viscous liquid. The coloration of the composition of Example 10 can range from clear to a blue color. In some embodiments, the composition of Example 10 has a water phase with a pH of 4.05.

In some embodiments, varying the percentage of various ingredients of the composition of Example 10 can produce formulations that form spheres for different periods of time when the composition is agitated.

For example, formulation A forms a composition that produces large sized spheres approximately 10-15 minutes after agitation. Formulation A is observed to begin separating out into the two phases approximately 30 minutes after agitation. Subsequently, formulation A completely separates 1 hour after agitation. In some embodiments, the viscosity of the Phase 1 water phase of formulation A is approximately 1400 cps.

In some examples, formulation B forms a composition that, when agitated, forms medium sized spheres within 5 minutes after agitation. Formulation B is observed to completely separate out into the two phases approximately 30 minutes after agitation. In some embodiments, the viscosity of the Phase 1 water phase of formulation B is approximately 520 cps.

In some examples, formulation C forms a composition that, when agitated, forms medium sized spheres within 2 minutes after agitation. Formulation C is observed to begin separating out into the two phases approximately 15 minutes after agitation. Formulation C is observed to separate faster than formulation B.

In some examples, formulation D forms a composition that, when agitated, forms medium sized spheres within 20 minutes after agitation. Formulation D is observed to begin separating 2 hours after agitation. After approximately 18-48 hours after agitation, the spheres are observed to form a top layer.

In some examples, formulation E forms a composition that forms medium sized spheres that begin to separate after approximately 3 minutes after agitation. Formulation E is observed as beginning to separate approximately 15 minutes after agitation. Formulation E completely separates out into two layers after approximately 30-40 minutes after agitation.

Example 11

| | Material | A wt % | B wt % | C wt % |
|---|---|---|---|---|
| | Phase 1 (Water) Phase | | | |
| 85° C. | Deionized water | Q.S. | Q.S. | Q.S. |
| Premix @ | Keltrol CG-T | 0.10 | 0.10 | 0.10 |
| 85° C. | Emery 917 | 1.00 | 1.00 | 1.00 |
| 85° C. | Amigel | 0.80 | 0.80 | 0.80 |
| 40° C. | Glypure L-70 | 8.00 | 8.00 | 8.00 |
| | NaOH @ 20% Solution | 10.00 | 10.00 | 10.00 |
| | Niacinamide PC | 2.00 | 2.00 | 2.0 |
| | Geogard Ultra | 1.00 | 1.00 | 1.00 |
| | Hydrolite-5 | 1.00 | 1.00 | 1.00 |
| | FD&C Yellow-5 @ 1% Solution | 0.40 | 0.28 | — |
| | FD&C Blue-1 @ 1% Solution | 0.013 | — | — |
| | Aquaspersabil BIO | — | — | 0.0166 |
| | Phase 2 (Anhydrous Phase) | | | |
| Premix at room temperature | Armesil 12C | 60.00 | 55.00 | 55.00 |
| | Botanisil GB-21 | 40.00 | 45.00 | 45.00 |

In some embodiments, the formulation of Example 11 is a mixture of Phase 1 (water phase) and Phase 2 (anhydrous phase). In some embodiments, the composition has a ratio of 70 wt. % of Phase 1 and 30 wt. % of Phase 2.

In some examples, the composition of Example 11 by mixing the Phase 1 water phase with the Phase 2 anhydrous Phase at slow mixing speeds, for example, at a rate of between 100-200 rpm. It is observed that higher sheer mixing speeds produce smaller spheres.

The produced composition forms a mixed bubble/sphere viscous serum. In some embodiments, the water phase has a pH of 4.1. In some examples, the viscosity of the water phase is 5000 cps while the viscosity of the anhydrous phase is 200 cps. In some embodiments, the coloration of formulations A, B, and C is as follows: formulation A is light amber, formulation B is gold champagne, and formulation C is black.

In some embodiments, the composition is stable after 3 months at a temperature of 50° C.

Example 12

A real-time stability study was conducted using the composition of Example 3. Following initial agitation, the sample was placed in long-term storage at room temperature. At 42 months, the sample was removed from storage and visually inspected. Upon visual inspection it was determined that the suspension of the anhydrous phase as spheres within the water phase was consistent with the suspension observed upon initial storage. The formulation had no noticeable phase separation or changes in sphere size, number or appearance between initial formulation and time point 42 months.

Example 13

A comparative study was conducted to compare the sphere breakage and total absorption time of the inventive composition to other known compositions. Compositions were manually applied to the skin and spread in a typical fashion, e.g. as one would apply a typical skin hydration lotion. The summarized data for the conducted study is provided below.

| Composition | Average Time to Sphere Breakage (seconds) | Average Difference from Inventive Compositions to Sphere Breakage | Average Time to Total Absorption | Average Difference from Inventive Compositions to Full Absorption |
|---|---|---|---|---|
| Proposed Inventive Compositions ("Brightening Spheres") | 1-2 | N/A | 32 | N/A |
| Unispheres (in a serum) | 15-20 | 13-19 | 37 | 5 |
| Unispheres (in a gel) | 5-10 | 3-9 | 48 | 16 |
| Argan Tra Beads (bead sizes 1.0-1.7 mm) | Did not break | Indefinite | 70 | 38 |
| Argan's Larger Beads (bead size 4 mm) | 5-10* | 3-9 | 70 | 38 |

*Beads broke quickly but took 5-10 seconds to disperse.

As demonstrated in Example 13, the spheres of the inventive compositions break apart more quickly than most comparable and competitive products. The average sphere breakage time is under 5 seconds, on average 1-2 seconds. Only one competitive product tested had a comparable sphere breakage time, though it took longer for the sphere content to actually disperse. In addition, the spheres inventive composition is absorbed into the skin within, on average, about 32 seconds. This is significantly faster than known comparable or competitive products, the closest comparable absorption rate of comparable products being 5 seconds slower, some comparable products taking close to 40 seconds longer to absorb.

Example 14

In one embodiment of the inventive formulation, the viscosity of the individual phases of the formulation, more specifically the water and the anhydrous phases, when in their separated state yield a composition with a lower viscosity than when the two phases are mixed together. In addition, a characteristic of the inventive formulation exemplified here is that the composition is capable of starting out in a state such that the water and anhydrous phases are separate, with the water phase being more dense and therefore separating to the bottom of an exemplary holding container, the viscosities of each phase being less than the viscosity of the mixed composition, resulting from the agitation of the composition and the formation of spheres of suspended anhydrous phase within the water phase.

Two exemplary compositions are provided below to demonstrate this effect:

| Formulation ID | Viscosity of Water Phase (cps) | Viscosity of Anhydrous Phase (cps) | Viscosity of Composition when Phases Combined |
|---|---|---|---|
| A | 3,000-5,000 | Nonviscous (under 400 cps) | 7,000-11,000 |
| B | 5,000-8,000 | Nonviscous (under 400 cps) | 13,000-22,000 | wherein Formulation ID "A" is the composition of Example 11A, and Formulation ID "B" is the composition of Example IC.

One of the beneficial aspects of the formulations described herein is that the duration of the formed spheres may be selectable based on the amounts and ratios of incorporated components, and such duration may be in excess of 3 years. However, if and when the composition does separate back out into its separate water and anhydrous phases, the composition is capable of returning to a state of lower viscosity. Such a cycle is repeatable.

Exemplary Aspects of the Invention

In order to further illustrate certain embodiments of the invention, a non-limiting list of various aspects of the invention is provided here:

1. A composition suitable for application to the skin as a cosmetic which is free of a film-forming emulsifier and comprises a first aqueous phase and a second anhydrous phase, the aqueous phase comprising 0.1-1.5% sclerotium gum, the anhydrous phase comprising one or more silicone or ester emollients having a viscosity of less than 500 cps and a hydrocarbon component composed of at least one of an aqueous-insoluble, silicone oil-soluble hydrocarbon having an 8-25 carbon backbone; the hydrocarbon being a branched hydrocarbon, a mixture of hydrolyzed, reduced, or hydrolyzed and reduced natural fatty acids, or a combination thereof; the first and second phases being in contact with one another and capable of existing in a first separated state and further capable of being modified to a second state upon agitation, the second state being such that the anhydrous phase is suspended in spheres within the aqueous phase and a majority of the spheres being capable of remaining stable in the second state for a period of at least 6 months without further agitation.
2. The composition of aspect 1, wherein the composition is emulsion-free and free from mannitol, lactose, cellulose, carbomer, cetearyl alcohol, emulsifying wax, lecithin, stearates, propylene glycol, polysorbates, polyethylene glycols, glycol-based preservatives, lipophilic gelling agents, a salt form of a neutralized acid in an amount greater than 0.5%, polyacrylates, and film-forming agents comprising at least one anionic polymer and at least one cationic polymer.
3. The composition of any one of aspects 1-2, wherein the composition can remain stable in the second state created upon agitation for a period of at least 18 months.
4. The composition of any one of aspects 1-2, wherein the composition can remain stable in the second state created upon agitation for a period of at least 36 months.
5. The composition of any one of aspects 1-4, wherein the composition comprises a second polysaccharide thickening agent in the aqueous phase which increases the percentage of light-transmittance of the composition compared to the percentage of light transmittance allowed by the composition when sclerotium gum is the sole thickening agent in the composition.
6. The composition of aspect 5, wherein the second polysaccharide is xanthan gum in an amount ranging from 0.1-2% by weight of the aqueous phase.
7. The composition of any one of aspects 1-6, wherein the light transmittance of the formulation in the second state is between 50-95%.
8. The composition of any one of aspects 1-7, wherein the composition comprises a water-soluble acid selected to confer a reduction in the speed of separation of the first aqueous phase and second anhydrous phase
9. The composition of aspect 8, wherein the water-soluble acid is an alpha hydroxy acid.
10. The composition of aspect 9, wherein the alpha hydroxy acid comprises glycolic acid in an amount between about 0.10-20% by weight of the aqueous phase of the composition.
11. The composition of any one of aspects 1-10, wherein the hydrocarbon has a density of less than 0.9 g/cm3 and is selected to manipulate the size and duration of formed spheres suspended within the aqueous phase when the composition is in the second state, with lower density hydrocarbons yielding a composition in which the duration of the spheres is shorter than when a higher density hydrocarbon is utilized.
12. The composition of aspect 11, wherein the hydrocarbon component is a branched hydrocarbon.
13. The composition of aspect 12, wherein none of the side chains of the branched hydrocarbon have a carbon backbone of more than four carbons.
14. The composition of any one of aspects 1-13, wherein the hydrocarbon comprises at least 4% by weight of the anhydrous phase isododecane, squalane, isohexadecane, or a mixture of any or all thereof.
15. The composition of any one of aspects 1-14, wherein the hydrocarbon is a mixture of hydrolyzed, reduced, or hydrolyzed and reduced natural fatty acids.
16. The composition of any one of aspects 1-15, wherein the hydrocarbon is coconut alkanes.
17. The composition of any one of aspects 1-16, wherein the hydrocarbon comprises isododecane in amount capable of contributing to the development of preferred size of formed spheres suspended within the aqueous phase when the composition is in the second state.

18. The composition of any one of aspects 1-17, wherein the silicone element of the anhydrous phase is a silicone oil comprising one or more of a siloxane or silane silicone, and is selected such that, in the first state, the composition comprises a water phase which is more dense than the anhydrous phase, thus in the separated state the aqueous phase of the composition lies beneath the anhydrous phase.

19. The composition of any one of aspects 1-18, wherein the silicone element of the anhydrous phase is selected such that the spheres of anhydrous phase suspended within the aqueous phase when the composition is in its second state are of a desired size.

20. The composition of any one of aspects 1-19, wherein the silicone element substantially comprises one or more of dimethicone, dimethicone crosspolymer, cyclopentasiloxane, cyclopentasiloxane blend, cyclohexasiloxane, cyclotetrasiloxane, cycloheptasiloxane, and phenyl trimethicone, and combinations of any or all thereof.

21. The composition according to any one of claims 1-20, wherein the spheres of anhydrous phase suspended within the aqueous phase lack a film barrier created by an emulsifying agent, except for any low or medium film barrier potentially contributed by the use of an ester emollient, polar molecules in a single molecular layer at the interface of the aqueous phase and the anhydrous phase, encapsulating the anhydrous phase and separating it from the aqueous phase.

22. The composition according to aspect 21, wherein the barrier thickness is less than that of the film formed when a film-forming emulsifier or solubilizer, e.g. a carbomer, is included in a formulation to form an emulsification.

23. The composition according to any one of aspects 1-22, wherein the composition comprises at least one glycol.

24. The composition of aspect 23, wherein the glycol detectably improves the absorption rate of the composition by the skin.

25. The composition of any one of claims 23-24, wherein the glycol is butylene glycol, pentylene glycol, or any combination of the two.

26. The composition of any one of aspects 23-25, wherein manual spreading of the composition on the skin results in the composition being absorbed by the skin within one minute without excessive rubbing, massaging, or application of excessive force typical of formulations which utilize bead, shell, or high film-forming formulations.

27. The composition of any one of aspects 1-26, wherein after absorption by the skin, the composition leaves no or a negligible amount of amount of residue on the skin surface such that any residue is unnoticeable to the feel as reported by a majority of users in a product skin test.

28. The composition according to any one of aspects 1-27, wherein the after application to the skin, the composition does not leave a sticky, tacky feel on the skin surface as measured by any standard measure of skin tackiness recognized in the art or reported by a majority of users in a test group.

29. The composition according to any one of aspects 1-28, wherein the viscosity of the aqueous phase ranges between 500-15,000 cps and the viscosity of the anhydrous phase of less than 10,000 cps. Alternatively, a composition of the invention can be characterized in having an aqueous phase with a viscosity of less than about 12,000 cps, such as less than about 10,000 cps and an oil phase with a viscosity of less than about 10,000 cps, such as less than about 5,000 cps, less than about 2,500 cps, or less than about 1,000 cps.

30. The composition according to any one of aspects 1-29, wherein the viscosity of the composition after mixing ranges from about 400 to about 25,000 cps.

31. The composition according to any one of aspects 1-30, wherein the pH of the composition after mixing is between about 3.0-6.0.

32. The composition according to any one of aspects 1-31, wherein the composition comprises a water soluble, broad spectrum preservative, free of polyethylene glycols (PEGs).

33. The composition according to any one of aspects 1-32 wherein the composition comprises a preservative in and capable of preserving the aqueous phase of the composition and containing one or more elements selected from the group comprising: propanediol, sodium benzoate, gluconolactone, calcium gluconate, potassium sorbate, lactic acid, 2-hydroxy-butanedioic acid, citric acid, hydroxy-acetic acid, 2,3-dihydroxy-(2R,3R)-butanedioic acid, phenoxyethanol, chlorphenesin, caprylyl glycol, caprylhydroxamic acid, glycerin, lactic acid, malic acid, citric acid, glycolic acid, ascorbic acid, tartaric acid, and gluconic acid.

34. The composition of any one of aspects 1-33, wherein the composition may optionally comprise one or more complexion brighteners such as but not limited to Neurocap, tri hydroxy benzoic acid alpha-glucosides (Brightenyl®), niacinamide, SpecWhite® Plus, or copper derivative.

35. The composition of any one of aspects 1-34, wherein the composition may optionally comprise one or more of the following: colorants or inorganic salt (such as but not limited to sodium hydroxide, aminomethyl propanol), mica, peptides, skin whiteners, botanical extracts, vitamins, retinoids or other active ingredients imparting preferred health or aesthetic attributes.

36. A method of delivering a composition to the skin, the composition comprising a first aqueous phase and a second anhydrous phase, the aqueous phase comprising sclerotium gum and one or more of a aqueous soluble acid selected for its ability to increase the density of the aqueous phase and for its ability to enhance the aesthetic appeal of the composition, the anhydrous phase comprising at least one of isododecane and isohexadecane and a low density silicone component, the first and second phases existing in a first separated state and, upon agitation, the anhydrous phase becoming suspended in spheres within the aqueous phase as a second state, the duration of the spheres being selectively adjusted based on the ratios of one or more aqueous phase or anhydrous components, and such that upon even delivery to the skin, the composition is absorbed by the skin with minimal rubbing within 30 seconds of application.

37. A method of preparing a composition comprising a first aqueous phase and a second anhydrous phase, the aqueous phase comprising 0.1-1.5% sclerotium gum and 1.00-20.00% of alpha hydroxyl acid, the anhydrous phase comprising at least one of a aqueous-insoluble, silicone oil-soluble, branched hydrocarbon having 8-25 carbon backbone and high spreadability characteristics, and a silicone component, wherein the first and second phases exist in a first separated state, and wherein the duration of suspended spheres of anhydrous phase formed within the aqueous phase when the composition is agitated is controllable based on at least one of the following factors: a) the amount of sclerotium gum, xanthan gum, or other thickeners; b) the amount of isododecane, isohexadecane, other branched hydrocarbons, and/or mixture of hydrolyzed, reduced, or hydrolyzed and reduced natural fatty acids in the anhydrous phase; c) the amount of and density of the selected silicone component; d) the ratio of multiple silicones within the silicone component; e) the combination, in varying ratios, of the conditioning agent(s) and silicone(s) in the composition; f) the percent-of-total-composition ratio of the aqueous phase to anhydrous phase.

38. The method of any one of aspects 36-37, where in the silicone component of the anhydrous phase is comprised of one or more of a siloxane or silane silicone.

39. The method of any one of aspects 36-38, wherein the duration of the suspended spheres of anhydrous phase formed within the aqueous phase upon agitation of the composition is controlled based on the combination, in varying ratios, of isododecane or isohexadecane with dimethicone or dimethicone crosspolymer.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein.

When the singular forms "a," "an" and "the" or like terms are used herein, they will be understood to include plural referents unless the context clearly dictates otherwise. Thus, for example, reference to "an agent" includes two or more agents, and the like. The word "or" or like terms as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a two-phase composition" include "instructing the administration of a two-phase composition." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

The invention claimed is:

1. A composition suitable for application to the skin or hair as a cosmetic comprising:
   A. an aqueous phase that makes up at least 25 wt. % of the composition, the aqueous phase comprising sclerotium gum in a concentration of 0.1-1.5 wt. % of the aqueous phase, a preservative component in an amount that detectably inhibits bacterial growth in the aqueous phase, and water, the water forming at least 55 wt. % of the aqueous phase; and
   B. an oil phase that makes up at least 10 wt. % of the composition, the oil phase comprising (a) an emollient component composed of one or more silicone emollients having a density of about 0.6 g/cm$^3$-about 0.9 g/cm$^3$ and (b) a hydrocarbon component composed of at least one of an aqueous-insoluble, silicone oil-soluble hydrocarbon having an 8-25 carbon backbone, the hydrocarbon being a branched hydrocarbon; a mixture of hydrolyzed, reduced, or hydrolyzed and reduced natural fatty acids; or a combination thereof;
   (i) the oil phase and aqueous phase together making up at least 85 wt. % of the composition, (ii) the oil and aqueous phases are in contact with one another and (1) spontaneously form a first state in which the entirety of the aqueous phase is separated from the oil phase except at the interface of the phases and (2) form a second state upon agitation in which a majority of the oil phase is suspended in a plurality of separated spherical portions within the aqueous phase, a majority of the spherical portions being stable in the second state for a period of at least 1 month without further agitation.

2. The composition of claim 1, wherein the viscosity of the aqueous phase is between 1,000-12,000 centipoise at room temperature and the viscosity of the oil phase is between 50-1,000 centipoise.

3. The composition of claim 2, wherein the total viscosity of the composition in the second state is between 2,000-38,000 centipoise.

4. The composition of claim 3, wherein the total viscosity of the composition in the second state is between 5,000-25,000 centipoise.

5. The composition of claim 4, wherein the viscosity of the aqueous phase is between 2,000-10,000 centipoise and the viscosity of the oil phase is between 50-500 centipoise.

6. The composition of claim 5, wherein the composition is free of any film forming polymers, film-forming emulsifiers other than any present ester emollient having film-forming properties, or other film forming agents.

7. The composition of claim 6, wherein the composition is free of any emulsifiers.

8. The composition of claim 7, wherein the composition is free of any carbomers, emulsifying waxes, lecithin, stearates, propylene glycol, polysorbates, polyethylene glycols, lipophilic gelling agents, and polyacrylates.

9. The composition of claim 8, wherein the composition contains no more than 0.5 wt. % of any cetearyl alcohol, mannitol, lactose, or salt forms of a neutralized acid.

10. The composition of claim 9, wherein the spherical portions remain stable in the second state for a period of at least 6 months without further agitating the composition after the initial agitation step.

11. The composition of claim 10, wherein the spherical portions remain stable in the second state for a period of at least 1 year without further agitating the composition after the initial agitation step.

12. The composition of claim 9, wherein the aqueous phase further comprises a polysaccharide thickening agent in the aqueous phase, which in combination with the sclerotium gum is present in an amount ranging from 0.15 to 1.5 wt. % of the aqueous phase, and wherein the composition has a greater light transmittance than a composition that is identical except for comprising a corresponding amount of sclerotium gum only in the aqueous phase.

13. The composition of claim 12, wherein the polysaccharide thickening agent is xanthan gum and the xanthan gum is present in an amount ranging from 0.1-2 wt. % of the aqueous phase.

14. The composition of claim 12, wherein the hydrocarbon component makes up at least 20 wt. % of the oil phase.

15. The composition of claim 14, wherein the hydrocarbon component is composed of a branched hydrocarbon comprising one or more side chains.

16. The composition of claim 15, wherein the majority of the side chains of the branched hydrocarbon are between 1-4 carbons in length.

17. The composition of claim 16, wherein the hydrocarbon component is composed of isododecane, squalane, isohexadecane, or a mixture of any or all thereof.

18. The composition of claim 14, wherein the hydrocarbon component is a mixture of hydrolyzed, reduced, or hydrolyzed and reduced natural fatty acids.

19. The composition of claim 14, wherein the aqueous phase comprises a water-soluble acid in an amount that is capable of detectably extending the time the composition is maintained in the second phase following agitation.

20. The composition of claim 19, wherein the water-soluble acid is an alpha hydroxy acid present in an amount between about 0.10-20 wt. % of the aqueous phase.

21. The composition of claim 14, wherein a majority of the silicone emollient is composed of dimethicone, dimethicone crosspolymer, cyclopentasiloxane, cyclopentasiloxane blend, cyclohexasiloxane, cyclotetrasiloxane, cycloheptasiloxane, and phenyl trimethicone, or a combination of any or all thereof.

22. The composition of claim 21, wherein the composition comprises a glycol in an amount that detectably improves the absorption of the composition into the skin when applied topically and at least 95% of an amount of the composition applied to the skin between 0.025-0.075 mL is capable of being absorbed into the skin within one minute of topical application without rubbing and without leaving any detectable residue on the skin as reported by a majority of users in a product test.

23. The composition of claim 1, wherein the composition comprises one or more functional components selected from the group consisting of colorants, mica, peptides, botanical extracts, brightening agents, vitamins, and retinoids capable of improving the appearance of the skin or hair of a user or the aesthetic attributes of the composition.

24. The composition of claim 13, wherein the hydrocarbon component makes up at least 20 wt. % of the oil phase and is selected from isodecane, isohexane, or a combination thereof and the composition is free of proteins, algae products, and algae extracts.

* * * * *